(12) United States Patent
Chiorini et al.

(10) Patent No.: US 7,419,817 B2
(45) Date of Patent: Sep. 2, 2008

(54) SCALABLE PURIFICATION OF AAV2, AAV4 OR AAV5 USING ION-EXCHANGE CHROMATOGRAPHY

(75) Inventors: John A. Chiorini, Silver Springs, MD (US); Nikola A. Kaludov, Washington, DC (US)

(73) Assignee: The United States of America as represented by the Secretary Department of Health and Human Services, NIH., Washington, DC (US)

( * ) Notice: Subject to any disclaimer, the term of this patent is extended or adjusted under 35 U.S.C. 154(b) by 977 days.

(21) Appl. No.: 10/166,347

(22) Filed: May 17, 2002

(65) Prior Publication Data
US 2004/0110266 A1 Jun. 10, 2004

(51) Int. Cl.
C12N 7/02 (2006.01)
(52) U.S. Cl. .............. 435/239; 435/235.1; 210/656; 210/661; 424/93.6
(58) Field of Classification Search .............. 435/235.1, 435/239; 210/656, 661; 424/93.6
See application file for complete search history.

(56) References Cited

U.S. PATENT DOCUMENTS

| | | | |
|---|---|---|---|
| 6,146,874 A * | 11/2000 | Zolotukhin et al. | ...... 435/235.1 |
| 6,180,613 B1 | 1/2001 | Kaplitt et al. | |
| 6,221,349 B1 | 4/2001 | Couto et al. | |
| 6,309,634 B1 | 10/2001 | Bankiewicz et al. | |
| 6,391,858 B2 | 5/2002 | Podsakoff et al. | |
| 6,468,524 B1 | 10/2002 | Chiorini et al. | |
| 6,485,976 B1 | 11/2002 | Nadler et al. | |
| 6,855,314 B1 | 2/2005 | Chiorini et al. | |
| 6,984,517 B1 | 1/2006 | Chiorini et al. | |
| 2002/0076754 A1 | 6/2002 | Sun et al. | |
| 2003/0228282 A1 | 12/2003 | Gao et al. | |
| 2004/0086490 A1 | 5/2004 | Chiorini et al. | |
| 2004/0115789 A1 | 6/2004 | Meruelo et al. | |
| 2005/0255089 A1 | 11/2005 | Chiorini et al. | |

FOREIGN PATENT DOCUMENTS

| | | |
|---|---|---|
| DE | 44 36 664 A1 | 7/1996 |
| EP | 1 310 571 | 5/2003 |
| WO | WO 93/24641 A | 12/1993 |
| WO | WO 95/11997 A | 5/1995 |
| WO | WO 96/00587 A | 1/1996 |
| WO | WO 96/15777 A | 5/1996 |
| WO | WO 96/18727 | 6/1996 |
| WO | WO 97/06272 | 2/1997 |
| WO | WO 98/11244 A | 3/1998 |
| WO | WO 98/41240 A | 9/1998 |
| WO | WO 98/45462 A | 10/1998 |
| WO | WO 99/61601 A | 12/1999 |
| WO | WO 00/26254 | 5/2000 |
| WO | WO 00/28061 | 5/2000 |
| WO | WO 01/70276 A | 9/2001 |
| WO | WO 01/83692 | 11/2001 |
| WO | WO 03/093479 | 11/2003 |
| WO | WO 2004/112727 A | 12/2004 |
| WO | WO 2005/017101 | 2/2005 |
| WO | WO 2005/056807 A | 6/2005 |
| WO | WO 2006/029196 | 3/2006 |
| WO | WO 2006/119432 | 11/2006 |

OTHER PUBLICATIONS

Alexander et al., "DNA-Damaging Agents Greatly Increase the Transduction of Nodividing Cells by Adeno-Associated Virus Vectors" *J. Virol.* 68(12):8282-8287, Dec. 1994.
Alisky et al., "Transduction of Murine Cerebellar Neurons with Recombinant FIV and AAV5 Vectors" *Mol. Neurosci.* 11(1221):2669-2673, Aug. 2000.
Auricchio et al., "A Single-Step Affinity Column for Purification of Serotype-5 Based Adeno-Associated Viral Vectors" *Mol Ther* 4(4):372-374, Oct. 2001.
Chiorini et al., "Cloning and Characterization of Adeno-Associated Virus Type 5" *J. Virol.* 73(2):1309-1319, Feb. 1999.
Chiorini et al., "Cloning of Adeno-Associated Virus Type 4 (AAV4) and Generation of Recombinant AAV4 Particles" *J. Virol.* 71(9):6823-6833, Sep. 1997.
Clark et al., "Highly Purified Recombinant Adeno-Associated Virus Vectors are Biologically Active and Free of Detectable Helper and Wild-Type Viruses" *Hum. Gene Ther.* 10:1031-1039, Apr. 10, 1999.
Flannery et al., "Efficient Photoreceptor-targeted Gene Expression in vivo by Recombinant Adeno-Associated Virus" *Proc Natl Acad Sci U S A* 94:6916-6921, Jun. 1997.
Kaludov et al., "Adeno-Associated Virus Serotype 4 (AAV4) and AAV5 Both Require Sialic Acid Binding for Hemagglutination and Efficient Transduction but Differ in Sialic Acid Linkage Specificity" *J. Virol*, 75(15):6884-6893, Aug. 2001.
Kaludov et al., "Scalable Purification of Adeno-Associated Virus Type 2, 4 or 5 Using Ion-Exchange Chromatography" *Human Gene Therapy* 13:1235-1243, Jul. 2002.
Kaplitt et al. "Long Term Gene Expression and Phenotypic Correction using Adeno-Associated Virus Vectors in the Mammalian Brain" *Nat. Gen.* 8:148-154, Oct. 1994.
McCown et al., "Differential and Persistent Expression Patterns of CNS Gene Transfer by an Adeno-Associated Virus (AAV) Vector" *Brain Res* 713:99-107 (1996).
O'Riordan et al., "Scalable Chromatographic Purification Process for Recombinant Adeno-Associated Virus (rAAV)" *J Gene Med* 2:444-454 (2000).
Russell et al., "Adeno-Associated Virus Vectors Preferentially Transduce Cells in S Phase" *Proc. Natl. Acad. Sci. USA* 91: 8915-8919, Sep. 1994.
Rutledge et al., "Infectious Clones and Vectors Derived Form Adeno-Associated Virus (AAV) Serotypes other Than AAV Type 2" *J. Virol.* 72:309-319, Jan. 1998.

(Continued)

*Primary Examiner*—L Blaine Lankford
(74) *Attorney, Agent, or Firm*—Needle & Rosenberg P.C.

(57) ABSTRACT

The present invention provides methods of purifying adeno-associated virus (AAV) particles. These AAV particles include AAV2, AAV4 and AAV5 particles. The present invention also provides AAV particles purified by the methods of the present invention.

55 Claims, 4 Drawing Sheets

OTHER PUBLICATIONS

Snyder et al., "Persistent and Therapeutic Concentrations of Human Factor IX in Mice after Hepatic Gene transfer of Recombinant AAV Vectors" *Nat Genet 16*:270-276, Jul. 1997.

Xiao et al., "Efficient Long-Term Gene Transfer into Muscle Tissue of Immunocompetent Mice by Adeno-Associated Virus Vector" *J. Virol.* 70(11):8098-8108, Nov. 1996.

Zolotukhin et al., "Recombinant Adeno-Associated Virus Purification using Novel Methods Improves Infections Titer and Yield" *Gene Ther.* 6: 973-985 (1999).

Alisky J.M. and Tolbert D.M., "Differential labeling of converging afferent pathways using biotinylated dextran amine and cholera toxin subunit B," 1994, *Journal of Neuroscience Methods*, 52:143-148.

Allen, J.M., Halbert, C.L. and Miller, A.D., "Improved adeno-associated virus vector production with transfection of a single helper adenovirus gene, E4orf6," 2000, *Mol Ther*, 1:88-95.

Arnberg, N., A. H. Kidd, K. Edlund, J. Nilsson, P. Pring-Akerblom, and G. Wadell, "Adenovirus type 37 binds to cell surface sialic acid through a charge-dependent interaction," 2002, *Virology*, 302:33-43.

Atchison, R. W., B. C. Casto, and W. M. Hammon, "Adenovirus-Associated Defective Virus Particles," 1965, *Science*, 149:754-756.

Bachmann, P.A., M.D. Hoggan, E. Kurstak, J.L. Melnick, H.G. Pereira, P. Tattersall, and C. Vago, "Parvoviridae: second report,"1979, *Interverology*, 11:248-254.

Bajocchi G, Feldman SH, Crystal RG, Mastrangeli A., "Direct in vivo gene transfer to ependymal cells in the central nervous system using recombinant adenovirus vectors," 1993, *Nat Genet*, 3:229-234.

Bantel-Schaal U, Delius H, Schmidt R, zur Hausen H., "Human adeno-associated virus type 5 is only distantly related to other known primate helper-dependent parvoviruses," 1999, *J Virol.*, 73(2):939-947.

Bantel-Schaal U, zur Hausen H., "Characterization of the DNA of a defective human parvovirus isolated from a genital site," 1984, *Virology*, 134(1):52-63, XP009028974.

Bantel-Schaal, U. and M. Stohr, "Influence of adeno-associated virus on adherence and growth properties of normal cells," 1992, *J. Virol.*, 66:773-779.

Bantel-Schaal, U., Hub, B. and Kartenbeck, J., "Endocytosis of adeno-associated virus type 5 leads to accumulation of virus particles in the Golgi compartment,"2002, *J Virol*, 76:2340-2349.

Bartlett JS, Kleinschmidt J., Boucher RC, and Samulski RJ, "Targeted adeno-associated virus vector transduction of nonpermissive cell mediated by a bispecific F(ab'gamma)$_2$ antibody," 1999, *Nat Biotechnol*, 17:181-186.

Bartlett JS, Samulski RJ, McCown TJ., "Selective and rapid uptake of adeno-associated virus type 2 in brain," 1998, *Hum Gene Ther*, 9(8):1181-1186.

Bartlett, J.S., Wilcher, R. and Samulski, R.J., "Infectious entry pathway of adeno-associated virus and adeno-associated virus vectors," 2000, *J Virol*, 74:2777-2785.

Ben-Israel, H. and Kleinberger, T., "Adenovirus and cell cycle control," 2002, *Front Biosci*, 7:d1369-1395.

Bergelson, JM, Cunningham JA, Droguett G., Kurt-Jones EA, Krithivas A., Hong JS, Horwitz MS, Crowell RL, and Finberg RW, "Isolation of a common receptor for Coxsackie B viruses and adenoviruses 2 and 5," 1997, *Science*, 275:1320-1323.

Berns, K. I., "Parvoviridae: the viruses and their replication," *In* F. B. N., K. D. M., and H. P. M. (ed.), *Fields virology*, 3rd ed. Lippincott-Raven Publishers, Philadelphia, PA, p. 2173-2197, date unknown.

Blacklow, et al., "Serologic Evidence for Human Infection With Adenovirus-Associated Viruses," 1968, *J NCI*, 40(2):319-327.

Blacklow, N.R., Hoggan, M.D. and Rowe, W.P. "Isolation of adenovirus-associated viruses from man," 1967, *Proc Natl Acad Sci U S A*, 58:1410-1415.

Bomsel M. Alfsen A, "Entry of viruses through the epithelial barrier: pathogenic trickery," 2003, *Nat Rev Mol Cell Biol*, 4:57-68.

Bomsel M, David V, "Mucosal gatekeepers: selecting HIV viruses for early infection," 2002, *Nat Med*, 8:114-116.

Bossis, I. and Chiorini, J.A., "Cloning of an Avian Adeno-Associated Virus (AAAV) and Generation of Recombinant AAAV Particles," 2003, *J Virol*, 77(12):6799-6810.

Burcin, M.M., O'Malley, B.W. and S.Y. Tsai, "A regulatory system for target gene expression," 1998, *Frontiers in Bioscience*, 3:c1-7.

Carter, B. J., B. A. Antoni, and D. F. Klessig, "Adenovirus containing a deletion of the early region 2A gene allows growth of adeno-associated virus eith decreased efficiency," 1992, *Virology*, 191:473-476.

Carter, B. J., C. A. Laughlin, L. M. de la Maza, and M. Myers, "Adeno-associated virus autointerference," 1979, *Virology*, 92:449-462.

Casto, B. C., R. W. Atchison, and W. M. Hammon, "Studies on the relationship between adeno-associated virus type 1 (AAV-1) and adenoviruses. I. Replication of AAV-1 in certain cell cultures and its effect on helper adenovirus," 1967a, *Virology*, 32:52-59.

Casto, B. C., J. A. Armstrong, R. W. Atchison, and W. M. Hammon, "Studies on the relationship between adeno-associated virus type 1 (AAV-1) and adenoviruses. II. Inhibition of adenovirus plaques by AAV; its nature and specificity," 1967b, *Virology*, 33: 452-458.

Chang, L.S. and Shenk, T., "The adenovirus DNA-binding protein stimulates the rate of transcription directed-by adenovirus and adeno-associated virus promoters," 1990, *J Virol*, 64:2103-2109.

Chang, L.S., Y. Shi, and T. Shenk, "Adeno-associated virus P5 promoter contains an adenovirus E1A-inducible element and a binding site for the major late transcription factor,"1989, *J. Virol.*, 63:3479-3488.

Chao H et al., "Several Log Increase in Therapeutic Transgene Delivery by Distinct Adeno-Associated Viral Serotype Vectors," 2000, *Molecular Therapy*, 2(6):619-623.

Chejanovsky, N. and B.J. Carter, "Replication of a human parvovirus nonsense mutant in mammalian cells containing an inducible amber suppressor," 1989a, *Virology*, 171:239-247.

Chejanovsky, N. and B.J. Carter, "Mutagenesis of an AUG condon in the adeno-associated virus rep gene: effects on viral DNA replication," 1989b, *Virology*, 173:120-128.

Chiorini JA, Afione S, Kotin RM, "Adeno-associated virus (AVV) type 5 Rep protein cleaves a unique terminal resolution site compared with other AAV serotypes," May 1999a, *J. Virol.*, 73(5):4293-4298.

Chiorini, J.A., C.M. Wendtner, E. Urcelay, B. Safer, M. Hallek, and R.M. Kotin, "High-efficiency transfer of the T cell co-stimulatory molecule B7-2 to lymphoid cells using high-titer recombinant adeno-associated virus vectors"1995, *Human Gene Therapy*, 6:1531-1541.

Chiorini, J.A., L. Yang, B. Safer, and R.M. Kotin, "Determination of adeno-associated virus Rep68 and Rep78 binding sites by random sequence oligonucleotide selection," 1995, *J. Virol.*, 69:7334-7338.

Chiorini, J.A., M.D. Weitzmen, R.A. Owens, E. Urcelay, B. Safer, and R.M. Kotin, "Biologically active Rep proteins of adeno-associated virus type 2 produced as fusion proteins in *Escherichia coli*," 1994a, *J. Virol.*, 68:797-804.

Chiorini, J.A., S.M. Wiener, R.M. Kotin, Owens, SRM Kyöstiö, and B. Safer, "Sequence requirements for stable binding and function of Rep68 on the adeno-associated virus type 2 inverted terminal repeats,"1994b, *J. Virol.*, 68:7448-7457.

Cohen-Salmon et al., "Targeted ablation of connexin26 in the inner ear epithelial gap junction network causes hearing impairment and cell death," 2002, *Curr Biol*, 12:1106-1111.

Coria et al., "Isolation and identification of a bovine adenovirus type 3 with an adenovirus-associated virus", 1978, *American Journal of Veterinary Research*, 39(12):1904-1906, XP009050511.

Crystal RG, "Transfer of genes to humans: early lessons and obstacles to success," 1995, *Science*, 270(5235):404-410.

Database EMBL, Entry GGACTAA, GenBank Accession No. M61166, Mar. 27, 1991, XP002125220, 1991.

Davidson BL, Doran SE, Shewach DS, Latta JM, Hartman JW, Roessler BJ., "Expression of *Escherichia coli beta*-galactosidase and rat HPRT in the CNS of *Macaca mulatta* following adenoviral mediated gene transfer,"1994, *Exp Neurol*, 125:258-267.

Davidson BL, Stein CS, Heth JA, Martins I, Kotin RM, Derksen TA, Zabner J, Ghodsi A, Chiorini JA, "Recombinant adeno-associated virus type 2, 4, and 5 vectors: Transduction of variant cell types and regions in the mammalian central nervous system," 2000, *Proc Natl Acad Sci U S A.*, 97(7):3428-3432.

Deonarain MP, "Ligand-targeted receptor-mediated vectors for gene delivery," 1998, *Molecular Conjugate Vectors*, 8(1):53-69.

Derby, M. L., M. Sena-Esteves, et al., "Gene transfer into the mammalian inner ear using HSV-1 and vaccinia virus vectors," 1999, *Hear Res*, 134(1-2):1-8.

Di Pasquale, G., Rzadzinska, A., Schneider, M.E., Bossis, I., Chiorini, J.A., Kachar, B., "A novel bovine virus efficiently transduces inner ear neuroepithelial cells," 2005 *Molecular Therapy*, Academic Press, 11(6):849-855, XP004908862.

Di Pasquale, G., and J. A. Chiorini, "PKA/PrKX activity is a modular of AVV/adenovirus interaction," 2003, *EMBO J*, 22:1716-1724.

Di Pasquale, G., B. L. Davidson, et al., "Identification of PDGFR as a receptor for AAV-5 transduction," 2003, *Nat Med*, 9(10):1306-1312.

Dixit, M., M.S. Webb, W.C. Smart, and S. Ohi, "Construction and expression of a recombinant adeno-associated virus that harbors a human *beta*-globin-encoding cDNA," 1991, *Gene*, 104:253-257.

Doll RF, Crandall JE, Dyer CA, Aucoin JM, Smith Fl., "Comparison of promoter strengths on gene delivery into mammalian brain cells using AAV vectors," 1996, *Gene Ther*, 3:437-447.

Duan, D., Yue Y., Yan Z., McCray PBJr, and Engelhardt JF., "Polarity influences the efficiency of recombinant adenoassociated virus infection in differentiated airway epithelia," 1998, *Hum Gene Ther*, 9:2761-2776.

During MJ, Symes CW, Lawlor PA, Lin J, Dunning J, Fitzsimons HL, Poulsen D, Leone P, Xu R, Dicker BL, Lipski J, Young D, "An oral vaccine against NMDAR1 with efficacy in experimental stroke and epilepsy," 2000, *Science*, 287:1453-1460.

During MJ, Xu R, Young D, Kaplitt MG, Sherwin RS, Leone P., "Peroral gene therapy of lactose intolerance using an adeno-associated virus vector," 1998, *Nat Med*, 4(10):1131-1135.

During MJ, Leone P, "Adeno-associated virus vectors for gene therapy of neurodegenerative disorders," 1995-96, *Clin Neurosci*, 3(5):292-300, XP-002125034.

Erles, K., Sebokova, P. and Schlehofer, J.R., "Update on the prevalence of serum antibodies (IgG and IgM) to adeno-associated virus (AAV)," 1999, *J Med Virol*, 59:406-411.

Fan D-S, Ogawa M, Fujimoto K-I, Ikeguchi K, Ogasawara Y, Urabe M, Nishizawa M, Nakano I, Yoshida M, Nagatsu I, Ichinose H, Nagatsu T, Kurtzman GJ, Ozawa K, "Behavioral recovery in 6-hydroxydopamine-lesioned rats by contransduction of striatum with tyrosine hydroxylase and aromatic L-amino acid decarboxylase genes using two separate adeno-associated virus vectors," 1998, *Hum Gene Ther*, 9:2527-2535.

Fisher, KJ, Jooss K., Alston, J., Yang Y., Haecker SE, High K., Pathak R., Raper SE, and Wilson JM, "Recombinant adeno-associated virus for muscle directed gene therapy," 1997, *Nat Med*, 3:306-312.

Fisher, R.E., H.D. Mayor, "The evolution of defective and autonomous parvoviruses," 1991, *J Theor Biol*, 149:429-439.

Flotte TR, Solow R, Owens RA, Afione S, Zeitlin PL, Carter BJ, "Gene expression from adeno-associated virus vectors in airway epithelial cells," 1992, *Am J Respir Cell Mol Biol*, 7(3):349-356; XP000609213.

Flotte, T.R., S.A. Afione, C. Conrad, S.A. McGrath, R. Solow, H. Oka, P.L. Zeitlin, W.B. Guggino, and B.J. Carter, "Stable in vivo expression of the cystic fibrosis transmembrane conductance regulator with an adeno-associated virus vector," 1993, *Proc. Natl. Acad. Sci.*, 90:10613-10617.

Flotte, T.R., S.A. Afione, R. Solow, M.L. Drumm, D. Markakis, W.B. Guggino, P.L. Zeitlin, and B.J. Carter, "Expression of the cystic fibrosis transmembrane conductance regulator from a novel adeno-associated virus promoter," 1993, *J Biol Chem*, 268:3781-3790.

Frolenkov GI, Belyantseva IA, Friedman TB, Griffith AJ, "Genetic insights into the morphogenesis of inner ear hair cells," 2004, *Nat Rev Genet*, 5:489-498.

Gao, G., L. H. Vandenberghe, M. R. Alvira, Y. Lu, R. Calcedo, X. Zhou, and J. M. Wilson, "Clades of Adeno-associated viruses are widely disseminated in human tissues," 2004, *J Virol*, 78:6381-6388.

Gao, G.P., Alvira, M.R. Wang, L., Calcedo, R., Johnston, J. and Wilson, J.M., "Novel adeno-associated viruses from rhesus monkeys as vectors for human gene therapy," 2002, *Proc Natl Acad Sci USA*, 99:11854-11859.

GenBank Accession No. AY186198.

Georg-Fries B. Biederlack S. Wolf J, zur Hausen H, "Analysis of proteins, helper dependence, and seroepidemiology of a new human parvovirus," *Virology*, 134(1):64-71, XP002027460.

Ghodsi A., Stein C., Derksen T., Martins I., Anderson RD, & Davidson BL, "Systemic hyperosmolality improves *beta*-glucuronidase distribution and pathology in murine MPS VII brain following intraventricular gene transfer," 1999, *Exp Neurol*, 160:109-116.

Ghodsi A., Stein, C., Derksen T., Yang, G., Anderson R.D., Davidson B.L., "Extensive *beta*-glucuronidase activity in murine central nervous system after adenovirus-mediated gene transfer to brain,"1998, *Hum Gene Ther*, 9:2331-2340.

Girod A., Ried M., Wobus C., Lahm H., Leike K., Klienschmidt J., Deleage G., and Hallek M., "Genetic capsid modifications allow efficient re-targeting of adeno-associated virus type 2," 1999, *Nat Med*, 5:1052-1056.

Grimm, D. and M. A. Kay, "From virus evolution to vector revolution: use of naturally occurring serotypes of adeno-associated virus (AAV) as novel vectors for human gene therapy," 2003, *Curr Gene Ther*, 3(4)::281-304.

Grimm D and Kem A, Rittner K Kleinschmidt JA, "Novel Tools for Production and Purification of Recombinant Adenoassociated Virus Vectors," 1998, *Human Gene Therapy*, 9:2745-2760.

Guy J., Qi X., Muzyczka N., and Hauswirth WW, "Reporter expression persists 1 year after adeno-associated virus-mediated gene transfer to the optic nerve," 1999, *Arch Ophthalmol*, 117:929-937.

Halbert CL, Standaert TA, Aitken ML, Alexander IE, Russell DW, and Miller AD, "Transduction by adeno-associated virus vectors in the rabbit airway: efficiency, persistence and readministration," 1997, *J. Virol.*, 71:5932-5941.

Halbert, C. L., J. M. Allen, and A. D. Miller, "Adeno-associated virus type 6 (AAV6) vectors mediate efficient transduction of airway epithelial cells in mouse lungs compared to that of AAV2 vectors," 2001, *J Virol*, 75:6615-6624.

He, D. Z., J. Zheng, et al., "Development of acetylcholine receptors in cultured outer hair cells," 2001, *Hear Res*, 162(1-2):113-125.

Hehir K.M., Armentano D., Cardoza L.M., Choquette T.L., Berthelette P.B., White G.A., Couture L.A., Everton M.B., Keegan J., Martin J.M., Pratt D.A., Smith M.P., Smith A.E., Wadsworth S.C., "Molecular characterization of replication-competent variants of adenovirus vectors and genome modifications to prevent their occurence," 1996, *J Virol*, 70(12):8459-8467.

Heister, T., Heid, I. Ackermann, M., Fraefel, C., "Herpes simplex virus type 1/adeno-associated virus hybrid vectors mediate site-specific integration at the adeno-associated virus preintegration site, AAVS1, on human chromosome 19," 2002, *J Virol*, 76(14):7163-7173.

Hermonat PL, Santin AD, De Greve J, De Rijcke M, Bishop BM, Han L, Mane M, Kokorina N, "Chromosomal latency and expression at map unit 96 of wild-type plus adeno-associated virus (AAV)/Neo vector and identification of p81, a new AAV transcriptional promoter," Nov.-Dec. 1999, *J Hum Virol.*, 2(6):359-368.

Hermonat, PL and N Muzyczka, "Use of adeno-associated virus as a mammalian DNA cloning vector: transduction of neomycin resistance into mammalian tissue culture cells," 1984, *Proc Natl Acad Sci USA*, 81:6466-6470.

Hermonat, P.L., M.A. Labow, R. Wright, K.I. Berns, and N. Muzyczka, "Genetics of adeno-associated virus: isolation and preliminary characterization of adeno-associated virus type 3 mutants," 1984, *J. Virol.*, 51:329-339.

Hoggan, M. D., N. R. Blacklow, and W. P. Rowe, "Sutdies of small DNA viruses found in various adenovirus preparations: physical, biological, and immunological characteristics," 1966, *Proc Natl Acad Sci USA*, 55:1467-1474.

Hoggan, M.D., "Adenovirus associated viruses," 1970, *Prog Med Virol*, 12:211-239.

Holt, J. R., "Viral-mediated gene transfer to study the molecular physiology of the Mammalian inner ear" 2002, *Audiol Neurootol*, 7(3):157-160.

Holt, J. R., D. C. Johns, et al., "Functional expression of exogenous proteins in mammalian sensory hair cells infected with adenoviral vectors," 1999, *J Neurophysiol*, 81(4):1881-1888.

Hsueh Y-P, Sheng M., "Regulated expression and subcellular localization of syndecan heparan sulfate proteoglycans and the syndecan-binding protein CASK/LIN-2 during rat brain development," 1999, *J Neurosci*, 19(17):7415-7425.

Hsueh Y-P, Yang F-C, Kharazia V, Naisbitt S, Cohen AR, Weinberg RJ, Sheng M, "Direct interaction of CASK/LIN-2 and syndecan heparan sulfate proteoglycan and their overlapping distribution in neuronal synapses," 1998, *J Cell Biol*, 142(1):139-151.

Hull, R. N., J. R. Minner, and J. W. Smith, "New viral agents recovered from tissue cultures of monkey kidney cells. I. Origin and properties of cytopathogenic agents S.V.1, S.V.2, S.V.4, S.V.5, S.V.6, S.V.11, S.V.12 and S.V.15," 1956, *Am J Hyg*, 63:204-215.

Hull, R. N., and J. R. Minner, "New viral agents recovered from tissue cultures of monkey kidney cells. II. Problems of isolation and identification," 1957, *Ann NY Acad Sci*, 67:413-423.

Hull, R. N., J. R. Minner, and C. C. Mascoli, "New viral agents recovered from tissue cultures of monkey kidney cells, III. Recovery of additional agents both from cultures of monkey tissues and directly from tissues and excreta," 1958, *Am J Hyg*, 68:31-44.

Hunter, L.A. and R.J. Samulski, "Colocalization of adeno-associated virus Rep and capsid proteins in the nuclei of infected cells," 1992, *J. Virol.*, 66:317-324.

Im DS, Muzyczka N, "Partial purification of adeno-associated virus Rep78, Rep52, and Rep40 and their biochemical characterization," 1992 Feb, *J. Virol.*, 66(2):1119-1128, XP002125031.

Inglis VI, Jones MP, Tse AD, Easton AS, "Neutrophils both reduce and increase permeability in a cell culture model of the blood-brain barrier," 2004, *Brain Res*, 998(2):218-229.

Ito, M. and H.D. Mayor, "Hemagglutinin of type 4 adeno-associated satellite virus," 1968, *J. Immunol*, 100:61-68.

Jaksch, M., K.D. Gerbitz, and C. Kilger, "Screening for mitochondrial DNA (mtDNA) point mutations using nonradioactive single strand conformation polymorphism (SSCP) analysis," 1995, *Clin. Biochem.*, 28:503-509.

Janik, J.E., M.M. Huston, K. Cho, and J.A. Rose, "Efficient syntheses of adeno-associated virus structural proteins requires both adenovirus DNA binding protein and VA I RNA," 1989, *Virology*, 168:320-329.

Jero J, Mhatre AN, Tseng CJ, Stern RE, Coling DE, Goldstein JA, Hong K, Zheng WW, Hoque AT, Lalwani AK., "Cochlear gene delivery through an intact round window membrane in mouse," 2001, *Hum Gene Ther*, 12(5):539-548.

Johansson CB, Momma S, Clarke DL, Risling M, Lendahl U, Frisen J, "Identification of a neural stem cell in the adult mammalian central nervous system," 1999, *Cell*, 96(1):25-34.

Kanzaki, S., K. Ogawa, et al., "Transgene expression in neonatal mouse inner ear explants mediated by first and advanced generation adenovirus vectors," 2002, *Hear Res*, 169(1-2):112-120.

Katano, Hisako; Afione S, Schmidt M, Chiorini JA, "Identification of adeno-associated virus contamination in cell and virus stocks by PCR," Apr. 2004, *Biotechniques*, 36(4):676-680, XP001207105.

Kelsell, D.P., Dunlop, J., Stevens, H.P., Lench, N.J., Liang, J.N., Parry, G., Mueller, R.F., Leigh, I.M., "Connexin 26 mutations in hereditary non-syndromic sensorineural deafness," 1997, *Nature*, 387(6628):80-83.

Kern, A., K. Schmidt, C. Leder, O. J. Muller, C. E. Wobus, K. Bettinger, C. W. Von der Lieth, J. A. King, and J. A. Kleinschmidt, "Identification of a heparin-binding motif on adeno-associated virus type 2 capsids," 2003, *J Virol*, 77:11072-11081.

Klein RL, Meyer EM, Peel AL, Zolotukhin S, Meyers C, Muzyczka N, King MA., "Neuron-specific transduction in the rat septophippocampal or nigrostriatal pathway by recombinant adeno-associated virus vectors," 1998, *Exp Nerol*, 150:183-194.

Kondo M., Finkbeiner WE, and Widdicombe JH., "Simple technique for culture of highly differentiated cells from dog tracheal epithelium," 1991, *Am.J.Physiol*, 261:L106-L117.

Kotin et al., "Organization of adeno-associated virus DNA in latently infected Detroit 6 cells," 1989, *Virology*, 170(2):460-467.

Kotin, R.M., M. Siniscalco, R.J. Samulski, X. Zhu, L. Hunter, C.A. Laughlin, S. McLauglin, N. Muzyczka, M. Rocchi, and K.I. Berns, "Site-specific integregation by adeno-associated virus," 1990, *Proc. Natl. Acad. Sci. USA*, 87:2211-2215.

Kovacs P, Pinter M, Csaba G, "Effect of glucosphingolipid synthesis inhibitor (PPMP and PDMP) treatment on *Tetrahymena pyriformis*: data on the evolution of the signaling system," 2000, *Cell Biochem Funct*, 18(4):269-280.

Kyo S, Nakamura M, Kiyono T, Maida Y, Kanaya T, Tanaka M, Yatabe N, Inoue M, "Successful immortalization of endometrial glandular cells with normal structural and functional characteristics," 2003, *Am J Pathol*, 163(6):2259-2269.

Kyostio SR, Owens RA, Weitzman MD, Antoni BA, Chejanovsky N, Carter BJ, "Analysis of adeno-associated virus (AAV) wild-type and mutant Rep proteins for their abilities to negatively regulated AAV $p_5$ and $p_{19}$ mRNA levels," 1994, *J Virol*, 68(5):2947-2957, XP-002125032.

Laughlin, C.A., M.W. Myers, D.L. Risin, B.J. Carter, "Defective-interfering particles of the human parvovirus adeno-associated virus," 1979, *Virology*, 94:162-174.

Laughlin, C.A., N. Jones, and B.J. Carter, "Effect of deletions in adenovirus early region 1 genes upon replication of adeno-associated virus," 1982, *J. Virol*, 41:868-876.

Lee K, Kim YG, Jo EC, "Shuttle PCR-based cloning of the infections adeno-associated virus type 5 genome," 2003, *J Virol Methods*, 111(2):75-84.

Li J, Samulski RJ, Xiao X, "Role for Highly Regulated *rep* Gene Expression in Adeno-Associated Virus Vector Production," 1997, *J Virol*, 71(7):5236-5243.

Li Duan, M., T. Bordet, et al., "Adenoviral and adeno-associated viral vector mediated gene transfer in the guinea pig cochlea," 2002, *Neuroreport*, 13(10):1295-1299.

Liang Y, Annan RS, Carr SA, Popp S, Mevissen M, Margolis RK, Margolis RU., "Mammalian homologues of the *Drosophila* slit protein are ligands of the heparan sulfate proteoglycan glypican-1 in brain," 1999, *J Biol Chem*, 274(25):17885-17892.

Lo WD, Qu G, Sferra TJ, Clark R, Chen R, Johnson PR., "Adeno-associated virus-mediated gene transfer to the brain: duration and modulation of expression," 1999, *Hum Gene Ther*, 10:201-213.

Luchsinger, E., Strobbe, R., Dekegel, D. and Wellemans, G., "Use of B-IV zonal rotor centrifugation as a simple tool for the separation of adeno-associated X 7 virus (AAVX 7) from helper adenoviruses," 1971, *Arch Gesamte Virusforsch*, 33:251-258.

Luchsinger, E., Strobbe, R., Wellemans, G., Dekegel, D. and Sprecher-Goldberger, S., "Haemagglutinating adeno-associated virus (AAV) in association with bovine adenovirus type 1," 1970, *Brief report. Arch Gesamte Virusforsch*, 31:390-392.

Luebke, A. E., J. D. Steiger, et al., "A modified adenovirus can transfect cochlear hair cells in vivo without compromising cochlear function," 2001, *Gene Ther*, 8(10):789-794.

Luebke, A. E., P. K. Foster, et al., "Cochlear function and transgene expression in the guinea pic cochlea, using adenovirus- and adeno-associated virus-directed gene transfer," 2001, *Hum Gene Ther*, 12:773-781.

Maeda Y, Ikeda U, Ogasawara Y, Urabe M, Takizawa T, Saito T, Colosi P, Kurtzman G, Shimada K, Ozawa K, "Gene transfer into vascular cells using adeno-associated virus (AAV) vectors," 1997, *Cardiovasc Res*, 35(3):514-521, XP-002125030.

Mandel RJ, Rendahl KG, Spratt SK, Snyder RO, Cohen LK, Leff SE., "Characterization of intrastriatal recombinant adeno-associated virus-mediated gene transfer of human tyrosine hydroxylase and human GTP-cyclohydrolase I in a rat model of Parkinson's disease," 1998, *J Neurosci*, 18(11):4271-4284.

McCarty, D.M., J. Pereira, I. Zolotukhin, X. Zhou, J.H. Ryan, and N. Muzyczka, "Identification of linear DNA sequences that specifically bind the adeno-associated virus Rep protein," 1994, *J. Virol.*, 68:4988-4997.

McPherson, R. A., L. J. Rosenthal, and J. A. Rose, "Human cytomegalovirus completely helps adeno-associated virus replication," 1985, *Virology*, 147:217-222.

Mendelson, E., J.P. Trempe, and B.J. Carter "Identification of the trans-acting Rep proteins of adeno-associated virus by antibodies to a synthetic oligopeptide," 1986, *J. Virol.*, 60:823-832.

Meyers, C., Mane, M., Kokorina, N. Alam, S. and Hermonat, P.L., "Ubiquitous human adeno-associated virus type 2 autonomously replicates in differentiating keratinocytes of a normal skin model," 2000, *Virology*, 272:338-346.

Mitrani E; Ziv T, Thomsen G, Shimoni Y, Melton DA, Bril A, "Activin can induce the formation of axial structures and is expressed in the hypoblast of the chick," 1990, *Cell*, 63(3):495-501.

Mizukami, H., N.S. Young, and K.E. Brown, "Adeno-associated virus type 2 binds to a 150-kilodalton cell membrane glycoprotein," 1996, *Virology*, 217:124-130.

Mori, S., L. Wang, T. Takeuchi, and T. Kanda, "Two novel adeno-associated viruses from cynomolgus monkey: pseudotyping characterization of capsid protein," 2004, *Virology*, 330:375-383.

Mouw, M.B. and Pintel, D.J., "Adeno-associated virus RNAs appear in a temporal order and their splicing is stimulated during coinfection with adenovirus," 2000, *J. Virol*, 74:9878-9888.

Muramatsu S-I, et al., "Nucleotide Sequencing and Generation of an Infectious Clone of Adeno-Associated Virus 3," 1996, *Virology*, 221:208-217, XP000608965.

Muster et al., "Physical Mapping of Adeno-Associated Virus Serotype 4 DNA" 1980, *J. Virol.*, 35(3):653-661; XP002058632.

Muzyczka, N, "Use of adeno-associated virus as a general transduction vector for mammalian cells," 1992, *Curr Top Microbiol Immunol*, 158:97-129.

Myrup, A.C., Mohanty, S.B. and Hetrick, F.M., "Isolation and characterization of adeno-associated viruses from bovine adenovirus types 1 and 2," 1976, *Am J Vet Res*, 37(8):907-910.

Naz, S., Griffit,h A.J., Riazuddin, S., Hampton, L.L., Battey, J.F. Jr, Khan, S.N., Riazuddin, S., Wilcox, E.R., Friedman, T.B., "Mutations of *ESPN* cause autosomal recessive deafness and vestibular dysfunction," 2004, *J Med Genet*, 41(8):591-595.

No D, Yao TP, Evans RM., "Ecdysone-inducible gene expression in mammalian cells and transgenic mice," 1996, *Proc Natl Acad Sci USA*, 93(8):3346-3351.

Ogston, P., K. Raj, and P. Beard, "Productive replication of adeno-associated virus can occur in human papillomavirus type 16 (HPV-16) episome containing keratinocytes and is augmented by the HPV-16 E2 protein," 2000, *J Virol*, 74:3494-3504.

Opie et al., "Identification of amino acid residues in the capsid proteins of adeno-associated virus type 2 that contribute to heparan sulfate proteoglycan binding," 2003, *J Virol*, 77:6995-7006.

Parks, W.P., J.L. Melnick, R. Rongey, and H.D. Mayor, "Physical assay and growth cycle studies of a defective adeno-satellite virus," 1967, *J. Virol.*, 1:171-180.

Podsakoff, G., K.K. Jr Wong, and S. Chatterjee, "Efficient gene transfer into nondividing cells by adeno-associated virus-based vectors," 1994, *J. Virol.*, 68:5656-5666.

Polishchuk R, Di Pentima A, Lippincott-Schwartz J, "Delivery of raft-associated, GPI-anchored proteins to the apical surface of polarized MDCK cells by a transcytotic pathway," 2004, *Nat Cell Biol*, 6(4):297-307.

Prasad KM, Zhou C, Trempe JP, "Characterization of the Rep78/adeno-associated virus complex," 1997, *Virology*, 229(1):183-192, XP-002125033.

Qing K, Mah C, Hansen J, Zhou S, Dwarki V, Srivastava A., "Human fibroblast growth factor receptor 1 is a co-receptor for infection by adeno-associated virus 2," 1999, *Nat Med*, 5(1):71-77.

Qui J, Brown KE., "Integrin *alphaVbeta*5 is not involved in adeno-associated virus type 2 (AAV2) infection," 1999, *Virology*, 264(2):436-440.

Rabinowitz et al., "Cross-Packaging of a Single Adeno-Associated Virus (AAV) Type 2 Vector Genome into Multiple AAV Serotypes Enables Transduction with Broad Specificity," 2002, *J Virol*, 76(2):791-801, XP002247245.

Rabinowitz JE, Bowles DE, Faust SM, Ledford JG, Cunningham SE, Samulski RJ., "Cross-dressing the virion: the transcapsidation of adeno-associated virus serotypes functionally defines subgroups," 2004, *J Virol*, 78(9):4421-4432.

Reddy, V. S., P. Natarajan, B. Okerberg, K. Li, K. V. Damodaran, R. T. Morton, C. L. Brooks, 3rd, and J. E. Johnson, "Virus Particle Explorer (VIPER), a website for virus capsid structures and their computational analyses," 2001, *J Virol*, 75:11943-11947.

Rich DP, Couture LA, Cardoza LM, Guiggio LM, Armentano D., Espino PC, Hehir K., Welsh MJ, Smith AE, and Gregory RJ, "Development and analysis of recombinant adenoviruses for gene therapy of cystic fibrosis," 1993, *Hum. Gene Ther.*, 4:461-476.

Richardson, W. D., and H. Westphal, "Requirement for either early region 1a or early region 1b adenovirus gene products in the helper effect for adeno-associated virus," 1984, *J. Virol*, 51:404-410.

Rose, J.A., M.D. Hoggan, F. Koczot, and A.J. Shatkin, "Genetic relatedness studies with adenovirus-associated viruses," 1968, *J. Virol.*, 2:999-1005.

Rosenfeld et al., "Adeno-associated viral vector gene transfer into leptomeningeal xenografts," 1997, *J Neuro-Oncology*, 34(2):139-144.

Ryan, J.H., S. Zolotukhin, and N. Muzyczka, "Sequence requirements for binding of Rep68 to the adeno-associated virus terminal repeats," 1996, *J. Virol.*, 70:1542-1553.

Rzadzinska, A. K., M. E. Schneider, et al., "An actin molecular treadmill and myosins maintain stereocilia functional architecture and self-renewal," 2004, *J Cell Biol*, 164(6):887-897.

Saffer, L. D., R. Gu, et al., "An RT-PCR analysis of mRNA for growth factor receptors in damaged and control sensory epithelia of rat utricles," 1996, *Hear Res*, 94(1-2):14-23.

Salo R. and Mayor H., "Structural Polypeptides and Parvoviruses," 1977,*Virology*, 78:340-345; XP002058634.

Samulski RJ, Chang LS, Shenk T, "Helper-free stocks of recombinant adeno-associated viruses: normal integration does not require viral gene expression," 1989, *J Virol.*, 63(9):3822-3828, XP000283071.

Samulski, R. J., and T. Shenk, "Adenovirus E1B 55-M$_r$ polypeptide facilitates timely cytoplasmic accumulation of adeno-associated virus mRNAs," 1988, *J Virol*, 62:206-210.

Samulski, R.J., K.I. Berns, M. Tan, and N. Muzyczka, "Cloning of adeno-associated virus into pBR322: rescue of intact virus from the recombinant plasmid in human cells," 1982, *Proc Natl Acad Sci USA*, 79:2077-2081.

Sanes JR, JLR Rubenstein, and JF Nicolas, "Use of a recombinant retrovirus to study post-implantation cell lineage in mouse embryos," 1986, *EMBO J*, 5:3133-3142.

Sanlioglu, S., Benson, P.K., Yang, J., Atkinson, E.M., Reynolds, T. and Engelhardt, J.F., "Endocytosis and nuclear trafficking of adeno-associated virus type 2 are controlled by rac1 and phosphatidylinositol-3 kinase activation," 2000, *J Virol*, 74:9184-9196.

Schinkel AH, "P-Glycoprotein, a gatekeeper in the blood-brain barrier,"1999, *Adv Drug Deliv Rev*, 36:179-194.

Schlehofer JR, Heibronn R, Georg-Fries B, zur Hausen H, "Inhibition of initiator-induced SV40 gene amplification in SV40-transformed Chinese hamster cells by infection with a defective parvovirus," 1983, *Int J Cancer*, 32(5):591-595, XP009010321.

Schlehofer, J. R., M. Ehrbar, and H. zur Hausen, "Vaccinia virus, herpes simplex virus, and carcinogens induce DNA amplification in a human cell line and support replication of a helpervirus dependent parvovirus," 1986, *Virology*, 152:110-117.

Schmidt M, Grot E, Cervenka P, Wainer S, Buck C, Chiorini JA, "Identification and characterization of novel adeno-associated virus isolates in ATCC virus stocks," 2006, *J Virol*, 80(10):5082-5085.

Schmidt et al., "Cloning and characterization of a bovine adeno-associated virus," 2004, *Journal of Virology*, 78(12):6509-6516, XP00233552.

Schneider, M. E., I. A. Belyantseva, et al., "Rapid renewal of auditory hair bundles," 2002, *Nature*, 418(6900):837-838.

Schwede, T., J. Kopp, N. Guex, and M. C. Peitsch, "SWISS-MODEL: An automated protein homology-modeling server," 2003, *Nucleic Acids Res*, 31:3381-3385.

Seiler MP, Miller AD, Zabner J, Halbert CL, "Adeno-associated virus types 4 and 6 use distinct receptors for cell entry," 2006, *Hum Gene Ther*, 17:10-19.

Seiler, M. P., C. L. Halbert, J. A. Chiorini, A. D. Miller, and J. Zabner, "AAV5 and AAV6 Mediate Gene Transfer to Human Airway Epthelia Via Different Receptors," 2002, *Mol Ther*, 5:S40.

Senapathy, P., J.D. Tratschin, and B.J. Carter, "Replication of adeno-associated virus DNA. Complementation of naturally occurring rep-mutants by a wild-type genome or an ori- mutant and correction of terminal palindrome deletions," 1984, *J Mol Biol*, 179:1-20.

Shou, J., J. L. Zheng, et al., "Robust generation of new hair cells in the mature mammalian inner ear by adenoviral expression of *Hath1*," 2003, *Mol Cell Neurosci*, 23(2):169-179.

Smith, R. H., S. A. Afione, et al., "Transposase-mediated construction of an integrated adeno-associated virus type 5 helper plasmid," 2002, *Biotechniques*, 33(1):204-206,208,210-211.

Sobkowicz, H. M., J. M. Loftus, et al., "Tissue culture of the organ of Corti," 1993, *Acta Otolaryngol Suppl*, 502:3-36.

Srivastava et al., "Nucleotide Sequence and Organization of the Adeno-Associated Virus 2 Genome," 1983, *J. Virol.*, 45(2):555-564; XP002058633.

Staecker H, Li D, O'Malley BW Jr, Van De Water TR., "Gene expression in the mammalian cochlea: a study of multiple vector systems," 2001, *Acta Otolaryngol*, 121(2):157-163.

Stracker, T. H., G. D. Cassell, P. Ward, Y. M. Loo, B. van Breukelen, S. D. Carrington-Lawrence, R. K. Hamatake, P. C. van der Vliet, S. K. Weller, T. Melendy, and M. D. Weitzman, "The Rep protein of adeno-associated virus type 2 interacts with single-stranded DNA-binding proteins that enhance viral replication," 2004, *J Virol*, 78:441-453.

Summerford C, Bartlett JS, Samulski RJ., "*AlphaVbeta5* integrin: a co-receptor for adeno-associated virus type 2 infection," 1999, *Nat Med*, 5(1):78-82.

Summerford, C. and R. J. Samulski, "Membrane-associated heparan sulfate proteoglycan is a receptor for adeno-associated virus type 2 virions," 1998, *J Virol*, 72(2):1438-1445.

Superti, F., M. L. Marziano, A. Tinari, and G. Donelli, "Effect of polyions on the infectivity of SA-11 rotavirus in LCC-MK2 cells," 1993, *Comp Immunol Microbiol Infect Dis*, 16:55-62.

Suzuki, H., Y. Katori, et al., "Carbohydrate distribution in the living utricular macula of the guinea pig detected by lectins," 1995, *Hear Res*, 87(1-2):32-40.

Teramoto, S., Bartlett JS, McCarty DXX, Samulski RJ, and Boucher RC, "Factors influencing adeno-associated virus-mediated gene transfer to human cystic fibrosis airway epithelial cells: comparison with adenovirus vectors," 1998, *J Virol*, 72:8904-8912.

Thomas CE, Storm TA, Huang Z, Kay MA, "Rapid uncoating of vector genomes is the key to efficient liver transduction with pseudotyped adeno-associated virus vectors," 2004, *J Virol*, 78(6):3110-3122.

Tratschin, J. D., M. H. West, T. Sandbank, and B. J. Carter, "A human parvovirus, adeno-associated virus, as a eucaryotic vector: transient expression and encapsidation of the procaryotic gene for chloramphenicol acetyltransferase," 1984, *Mol Cell Biol*, 4:2072-2081.

Tratschin, J.D., I.L. Miller, and B.J. Carter, "Genetic analysis of adeno-associated virus: properties of deletion mutants constructed in vitro and evidence for an adeno-associated virus replication function," 1984, *J. Virol.*, 51:611-619.

Trempe, J.P. and B.J. Carter, "Regulation of adeno-associated virus gene expression in 293 cells: control of mRNA abundance and translation," 1988, *J. Virol.*, 62:68-74.

Trempe, J.P., E. Mendelson, and B.J. Carter, "Characterization of adeno-associated virus rep proteins in human cells by antibodies raised against rep expressed in *Escherichia coli*," 1987, *Virology*, 161:18-28.

Tuma PL and Hubbard AL, "Transcytosis: crossing cellular barriers," 2003, *Physiol Rev*, 83(3):871-932.

Voutetakis A, Kok MR, Zheng C, Bossis I, Wang J, Cotrim AP, Marracino N, Goldsmith CM, Chiorini JA, Loh YP, Nieman LK, Baum BJ, "Reengineered salivary glands are stable endogenous bioreactors for systemic gene therapeutics," 2004, *Proc Natl Acad Sci USA*, 101(9):3053-3058.

Walsh, C.E., J.M. Liu, X. Xiao, N.S. Young, A.W. Nienhuis, and R.J. Samulski, "Regulated high level expression of a human gamma-globin gene introduced into erythroid cells by an adeno-associated virus vector," 1992, *Proc Natl Acad Sci USA*, 89:7257-7261.

Walters, R.W., Yi, S.M. Keshavjee, S., Brown, K.E., Welsh, M.J., Chiorini, J.A. and Zabner, J., "Binding of adeno-associated virus type 5 to 2,3-linked sialic acid is required for gene transfer," 2001, *J Biol Chem*, 276:20610-20616.

Walters, RW, Duan D., Engelhardt JF, and Welsh MJ., "Incorporation of adeno-associated virus in a calcium phosphate coprecipitate improves gene transfer to airway epithelia in vitro and in vivo," 2000, *J. Virol.*, 74:535-540.

Walters, RW, Grunst T., Bergelson JM, Finberg RW, Welsh MJ, and Zabner J., "Basolateral localization of fiber receptors limits adenovirus infection from the apical surface of airway epithelia," 1999, *J. Biol. Chem.*, 274:10219-10226.

Walz, C., A. Deprez, T. Dupressoir, M. Durst, M. Rabreau, and J. R. Schlehofer, "Interaction of human papillomavirus type 16 and adeno associated virus type 2 co-infecting human cervical epithelium," 1997, *J Gen Virol*, 78(Pt 6):1441-1452.

Wang G., Davidson BL, Melchert P., Slepushkin VA, van Es HH, Bodner M., Jolly DJ, and McCray PB Jr., "Influence of cell polarity on retrovirus-mediated gene transfer to differentiated human airway epithelia," 1998, *Journal of Virology*, 72:9818-9826.

Wang X S, and A Srivastava, "Resue and autonomous replication of adeno-associated virus type 2 genomes containing Rep-binding site mutations in the viral p5 promoter," 1998, *J Virol*, 72:4811-4818.

Ward, P., F. B. Dean, M. E. O'Donnell, and K. I. Berns, "Role of the adenovirus DNA-binding protein in in vitro adeno-associated virus DNA replication," 1998, *J Virol*, 72:420-427.

Weindler, F. W., and R. Heilbronn, "A subset of herpes simplex virus replication genes provides helper functions for productive adeno-associated virus replication," 1991, *J Virol*, 65:2476-2483.

Winocour, E., M.F. Callaham, and E. Huberman, "Perturbation of the cell cycle by adeno-assocated virus," 1988, *Virology*, 167:393-399.

Xiao, W., N. Chirmule, S. C. Berta, B. McCullough, G. Gao, and J. M. Wilson, "Gene therapy vectors based on adeno-associated virus type 1," 1999, *J Virol*, 73:3994-4003.

Xiao Xm Li J, Samulski RJ, "Production of High-Titer Recombinant Adeno-Associated Virus Vectors in the Absence of Helper Adenovirus," 1997, *J Virol*, 72(3):2224-2232.

Xie Q. and Chapman MS, "Canine parvovirus capsid structure, analyzed at 2.9 Å resolution," 1996, *J Mol Biol*, 264:497-520.

Yalkinoglu, A.O., Heilbronn, R., Burkle, A., Schlehofer, J.R. and zur Hausen, H., "DNA amplification of adeno-associated virus as a response to cellular genotoxic stress," 1988, *Cancer Res*, 48:3123-3129.

Yakobson, B., Hrynko, T.A., Peak, M.J. and Winocour, E., "Replication of adeno-associated virus in cells irradiated with UV light at 254 nm," 1989, *J Virol*, 63:1023-1030.

Yamano, S., Huang, L.Y., Ding, C., Chiorini, J.A., Goldsmith, C.M., Wellner, R.B., Golding, B., Kotin, R.M., Scott, D.E. and Baum, B.J., "Recombinant adeno-associated virus serotype 2 vectors mediate stable interleukin 10 secretion from salivary glands into the bloodstream," 2002, *Hum Gene Ther*, 13:287-298.

Yamaya, M., Finkbeiner WE, Chun SY, and Widdicombe JH, "Differentiated structure and function of cultures from human tracheal epithelium," 1992, *Am.J.Physiol*, 262:L713-L724.

Zabner J, Seiler M, Walters R, Kotin RM, Fulgeras W, Davidson BL, Chiorini JA, "Adeno-associated virus type5 (AAV5) but not AAV2 binds to the apical surfaces of airway epithelia and facilitates gene transfer," 2000, *J Virol.*, 74(8):3852-3858, XP002197205.

Zabner, J., Zeiher BG, Friedman E, and Welsh MJ, "Adenovirus-mediated gene transfer to ciliated airway epithelia requires prolonged incubation time,"1996, *J. Virol.*, 70:6994-7003.

Zhang JR, Mostov KE, Lamm ME, Nanno M, Shimida S, Ohwaki M, Tuomanen E, "The polymeric immunoglobulin receptor translocates pneumococci across human nasopharyngeal epithelial cells," 2000, *Cell*, 102(6):827-837.

Zhu ZB, Makhija SK, Lu B, WAng M, Rivera AA, Preuss M Zhou F, Siegal GP, Alvarez RD, Curiel DT, "Transport across a polarized monolayer of Caco-2 cells by transferrin receptor-mediated adenovirus transcytosis," 2004, *Virol*, 325:116-128.

\* cited by examiner

SCALABLE PURIFICATION OF AAV2, AAV4 OR AAV5 USING ION-EXCHANGE CHROMATOGRAPHY

FIELD OF THE INVENTION

The present invention relates to the purification of AAV2, AAV4 and AAV5 utilizing ion-exchange chromatography.

BACKGROUND

The availability of high titer, high purity, AAV2 stocks has dramatically increased the understanding of this virus and its utility as a gene transfer vector. The rapid development of adeno-associated virus type 2 (AAV2) as a vector system is the result of improvements in the production and purification of the virions. Gene-transfer vectors based on AAV have gained popularity due to a combination of attractive features. Wild type AAV is naturally defective for replication and considered to be nonpathogenic. Recombinant AAV vectors do not contain viral genes and can transduce both mitotic and post-mitotic cells (Alexander et al., 1994; Kaplitt et al., 1994; Russell et al., 1994; McCown et al., 1996). Efficient long-term gene transfer has been reported in a number of cell types including eye, CNS, and muscle (McCown et al., 1996; Xiao et al., 1996; Flannery et al., 1997; Snyder et al., 1997). Most pre-clinical studies and current Phase I clinical trials use vectors derived from AAV2. However, vectors derived from other AAV serotypes such as AAV4 and AAV5 have proven to be more efficient in transducing certain cell types than AAV2 and could be resistant to neutralizing antibodies against AAV2 (Rutledge et al., 1998). The difference in transduction efficiencies for these serotypes appears to be the result of different mechanisms of uptake (Chiorini et al., 1997; Chiorini et al., 1999). Therefore, gene therapy vectors based on other serotypes of AAV may be useful for transducing cell types that are not efficiently transduced by AAV2 or when there are neutralizing antibodies against AAV2.

Recent advances in the production and purification of high titer rAAV vector stocks have facilitated the transition to human clinical trials. The use of affinity chromatography based on AAV2s interaction with heparin sulfate has replaced density gradient centrifugation for purification of rAAV2. Additional improvements in rAAV stock preparations include the use of deoxycholate treatment of the cell lysate, iodixanol gradient separation prior to the affinity chromatography, have resulted in high titer rAAV2 (Clark et al., 1999; Zolotukhin et al., 1999). While this method is a significant improvement over CsCl gradient centrifugation alone, the procedure results in recovery of less than 50% of the starting transducing virus. The preparation also contains a significant percentage of empty particles, which could decrease the therapeutic index of the preparation. O'Riordan et al. have developed a scalable two-step purification procedure using ion-exchange chromatography followed by sulphate affinity chromatography (O'Riordan et al., 2000). However, not all AAV serotypes bind to heparan sulfate on the cell surface. Transduction with either AAV4 or AAV5 is insensitive to heparin sulfate competition, indicating distinct interactions for these serotypes. Instead, both AAV4 and AAV5 require sialic acid on the cell surface for binding and transduction (Kaludov et al., 2001). Thus the affinity chromatography approach used for AAV2 will not be useful for purifying these isolates.

The present invention provides a simple ion exchange method for purifying different AAV serotypes (AAV2, 4 and 5) that does not rely on the affinity of the virus for heparin sulfate or sialic acid. The procedure is fast, reproducible, efficient, and yields highly purified rAAV. It is also easily amenable for large-scale production of clinical grade vector. The final rAAV stock consists primarily of full particles as analyzed by electron microscopy. HPLC-purified virus also shows an improved particle-to-infectivity ratio compared to virus purified by conventional CsCl density gradients. This new purification method will facilitate high titer, high purity production of rAAV4 and rAAV5 and will further their development as gene transfer vectors for clinical applications.

SUMMARY OF THE INVENTION

The present invention provides a method of purifying adeno-associated virus (AAV) particles using high performance liquid chromatography (HPLC). The AAV particles may be wildtype or recombinant AAV. HPLC is carried out using ion exchange media equilibrated at a pH in the range of about 5.5 to about 7.5 depending on the type of ion exchange column utilized.

The present invention provides a method of purifying adeno-associated virus (AAV) particles comprising: a) subjecting a culture of wild-type or recombinant AAV particles to high performance liquid chromatography (HPLC), wherein the particles are bound to an ion exchange column equilibrated at a pH of about 6.0 to about 7.2 and at a salt concentration of greater than 100 mM, and wherein the AAV particles are eluted with about 100-600 mM salt in order to obtain purified AAV particles; b) concentrating the eluted AAV particles; and c) washing the concentrated AAV particles.

Also provided by this invention is a method of purifying adeno-associated virus (AAV) particles comprising: a) treating a culture of wild-type or recombinant AAV with a detergent; b) subjecting the culture of (a) to high performance liquid chromatography (HPLC), wherein the particles are bound to an ion exchange column equilibrated at a pH of about 6.0 to about 7.2 and at a salt concentration of greater than 100 mM and wherein the AAV particles are eluted with about 150-500 mM salt in order to obtain purified AAV particles; c) concentrating the eluted AAV particles; and d) washing the concentrated AAV particles.

The present method also provides a method of purifying AAV2 particles comprising: a) treating a culture of wild-type or recombinant AAV2 particles with at least about 0.5% deoxycholate (DOC) and; b) subjecting the culture of (a) to high performance liquid chromatography (HPLC), wherein the particles are bound to a CM-Poros column equilibrated at a pH of about 5.5 to about 7.5 and at a salt concentration of greater than 150 mM and wherein the AAV particles are eluted with about 100-400 mM salt in order to obtain purified AAV particles.

Further provided by the present invention is a method of purifying AAV2 particles comprising: a) treating a culture of wild-type or recombinant AAV2 particles with at least about 0.5% deoxycholate (DOC) and; b) subjecting the culture of (a) to high performance liquid chromatography (HPLC), wherein the particles are bound to an HQ column equilibrated at a pH of about 6.5 to about 7.5 and at a salt concentration of greater than 150 mM and wherein the AAV particles are eluted with about 100-300 mM salt in order to obtain purified AAV particles.

Also provided is a method of purifying AAV4 particles comprising: a) treating a culture of wild-type or recombinant AAV4 particles with at least about 0.5% octylglucopyranoside (OCG) and benzonase; and b) subjecting the culture of (a) to high performance liquid chromatography (HPLC), wherein the particles are bound to an HQ column equilibrated at a pH of about 6.5 to about 7.5 and at a salt concentration of greater than 150 mM, and wherein the AAV 4 particles are eluted with about 200-600 mM salt in order to obtain purified AAV 4 particles.

DETAILED DESCRIPTION OF THE INVENTION

Figure 1:
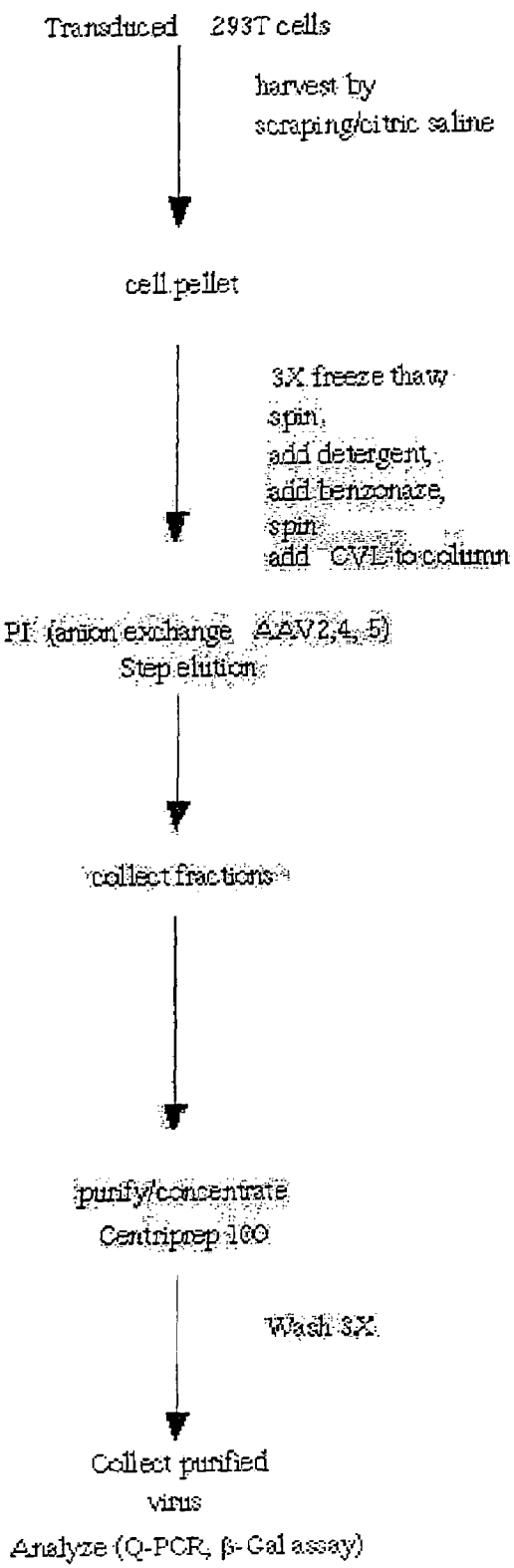
FIG. 1 shows a scheme for AAV2, 4 and 5 Purification. 293T cells were triple transfected with AAV helper, vector, and Adenoviral helper plasmids as described in the Examples. Forty-eight hours post transfection the cells were harvested and the lysate processed as described in FIG. 1 and fractionated on PI resin at either pH 6.7, 7.0, or 6.2 for AAV2, 4,or 5 respectively. Fractions were eluted with KCl and the fractions with peak biological activity were collected, pooled, and concentrated/dialyzed using Centriplus 100 filters.

The present invention may be understood more readily by reference to the following detailed description of the preferred embodiments of the invention.

Before the present methods are disclosed and described, it is to be understood that this invention is not limited to specific constructs, molecules and methods, as such may of course, vary. It is also to be understood that the terminology used herein is for the purpose of describing particular embodiments only and is not intended to be limiting.

It must be noted that, as used in the specification and the appended claims, the singular forms "a," "an," and "the" include plural referents unless the context clearly dictates otherwise. For example, a particle can mean a single particle or more than one particle.

The present invention provides a method of purifying adeno-associated virus (AAV) particles comprising: a) subjecting a culture of wild-type or recombinant AAV particles to high performance liquid chromatography (HPLC), wherein the particles are bound to an ion exchange column equilibrated at a pH of about 6.0 to about 7.2 and at a salt concentration of greater than 100 mM and wherein the AAV particles are eluted with about 100-600 mM salt in order to obtain purified AAV particles. This method can further comprise a concentration step and a washing step.

Therefore, the present invention also provides a method of purifying adeno-associated virus (AAV) particles comprising: a) subjecting a culture of wild-type or recombinant AAV particles to high performance liquid chromatography (HPLC), wherein the particles are bound to an ion exchange column equilibrated at a pH of about 6.0 to about 7.2 and at a salt concentration of greater than 100 mM and wherein the AAV particles are eluted with about 100-600 mM salt in order to obtain purified AAV particles; c) concentrating the eluted particles; and d) washing the particles.

In the methods of the present invention, cultures of AAV particles are obtained by methods standard in the art (Chiorini et al. (1997) and Chiorini et al. (1999)) and as described in the Examples included herein. The AAV particles of this invention can be AAV1 particles, AAV2 particles, AAV3 particles, AAV4 particles, AAV5 particles or AAV6 particles.

Standard methods for performing HPLC are well known to those of ordinary skill in the art. The ion exchange columns that can be utilized in the methods of the present invention include both cationic and anionic ion exchange columns. Weak cationic and strong cationic ion exchange columns can also be used in the methods of this invention. Strong cationic exchange columns can have a surface coated with a polyhydroxylated polymer and functionalized with sulfopropyl, a dextran matrix functionalized with a sulfopropyl group, or a surface coated with a polyhydroxylated polymer functionalized with sulfoethyl. Examples of strong cationic ion exchange columns using each of these materials include, respectively, a POROS HS™, a SP-Sephadex™ column and a POROS S™ column.

Weak cationic exchange columns can have a dextran matrix functionalized by carboxymethyl or an acrylic matrix functionalized by a carboxylic group. Examples of weak cationic exchange columns using each of these materials include, respectively, CM-Sephadex™ and Bio-Rex 70™.

Weak anionic and strong anionic ion exchange columns can also be used in the methods of the present invention. Weak anionic ion exchange columns can have a surface coated with polyethyleneimine that is capable of surface ionization up to a pH of about 9, a styrene-divinylbenzene copolymer containing sulfonic acid groups or a dextran matrix functionalized by diethylaminoethyl. Examples of weak anionic exchange columns using each of these materials include, respectively, a POROS PI™ column, a Dowex 50™ column and a DEAE-Sephadex™. Strong anionic exchange columns can have a surface coated with quaternized polyethyleneimine with a surface ionization over a pH range of about 1 to about 14. An example of a such a strong anionic ion exchange column is a POROS HQ™ column. The resins for the columns listed above can be obtained from Amersham/Pharmacia (Piscataway, N.J.), PerSeptive Biosystems (Foster City, Calif.), TosoHaas (Montgomeryville, Pa.) and other suppliers.

The column can be a 0.5 ml column, a 1.5 ml column, a 10 ml column, a 20 ml column, a 30 ml column, a 50 ml column, a 100 ml column, a 200 ml column, a 300 ml column, a 400 ml column, a 500 ml column, a 600 ml column, a 700 ml column, an 800 ml column, a 900 ml column, a 1000 ml (1L) column a 2000 ml (2L) a 10L column, a 20L column, a 30L column, a 40L column, a 50L column, a 60L column, a 70L column, an 80L column a 90L column, a 100L column or a column with a capacity greater than 100L as well as any other column with a capacity between the volumes listed above.

In the methods of the present invention, the ion exchange column can be equilibrated at a pH ranging from about 6.0 to about 7.2 and at a salt concentration that can range from about 100 mM to 200 mM. Therefore, the column can be equilibrated at a pH of about 6.0, 6.1, 6.2, 6.3, 6.4, 6.5, 6.6, 6.7, 6.8, 6.9, 7.0, 7.1, 7.2 or any other pH in between these pH values and at a salt concentration of about 100 mM, 125 mM, 150 mM, 175 mM, 200 mM or any other concentration in between the salt concentration values listed above. The salts that can be utilized to equilibrate the column include NaCl, KCl or any other salt that can be adjusted to match the ionic strength of KCl.

In the methods of the present invention, the AAV particles can be eluted with KCl. The salt concentration utilized to elute the particles can range from about 100 mM to about 600 mM. Therefore, the salt concentration utilized to equilibrate the column can be about 100 mM, 125 mM, 150 mM, 175 mM, 200 mM, 225 mM, 250mM, 275 mM, 300 mM, 325 mM, 350 mM, 375 mM, 400 mM, 425 mM, 450 mM, 475 mM, 500 mM, 525 mM, 550 mM, 575 mM, 600 mM or any other salt concentration in between the salt concentration values listed above. Other salts, such as NaCl can be utilized for elution as long as the salt concentration is adjusted to match the ionic strength of KCl.

In order to concentrate eluted AAV particles, any concentration membrane capable of retaining a 26 nm particle or possessing a 100,000 MW cutoff can be utilized. For the concentration step, many membranes and devices that are known in the art can be used, such as the UltraLab tangential flow system (Pall Filtron). Membranes that will retain a 20 nm particle such as the Omega 100VR (Pall Filtron) or 100 or 300 kDa Biomax membranes from Amicon or the 100 kDa YM membrane (regenerated cellulose) from Amicon found in the Amicon Cetriprep plus filters can be used in these devices.

The particles eluted, or eluted and concentrated utilizing the methods of the present invention can be washed with a buffer containing about 150 mM salt. The washing buffer will typically comprise about 20 mM Tris, about 150 mM NaCl, about 1 mM MgCl and about 5 mM CaCl. The washing step can be repeated as many times as one of ordinary skill in the art deems necessary to obtain the level of purity desired.

In all of the methods of the present invention, the culture of wild-type or recombinant AAV particles can be applied to a negative column prior to subjecting the culture to HPLC in order to remove contaminating proteins. Columns that can be utilized as a negative column include, but are not limited to, a hydrophobic column, and ion exchange columns that do not bind virus under the lysis conditions described in this method.

The present invention also provides a method of purifying adeno-associated virus (AAV) particles comprising: a) treating a culture of wild-type or recombinant AAV particles with a detergent and; subjecting the culture of (a) to high performance liquid chromatography (HPLC), wherein the particles are bound to an ion exchange column equilibrated at a pH of about 6.0 to about 7.2 and at a salt concentration of greater than 150 mM and wherein the AAV particles are eluted with about 100-600 mM salt in order to obtain purified AAV particles.

The present invention also provides a method of purifying adeno-associated virus (AAV) particles comprising: a) treating a culture of wild-type or recombinant AAV with a detergent; b) subjecting the culture of (a) to high performance liquid chromatography (HPLC), wherein the particles are bound to an ion exchange column equilibrated at a pH of about 6.0 to about 7.2 and at a salt concentration of greater than 150 mM and wherein the AAV particles are eluted with about 100-600 mM salt in order to obtain purified AAV particles; c) concentrating the eluted particles; and d) washing the particles.

Although it is not necessary to treat cultures of AAV particles with a detergent in order to purify the particles according to the methods of the present invention, the invention also contemplates treating the culture of AAV particles with a detergent prior to purification. Treatment of the culture with a detergent improves the yield of active virus in the CLV by dissociating the viral particles from the cellular debris. Detergent also acts to alter the surface charge of proteins and affects their interaction with ion exchange chromatography resins. Thus, if a step of detergent exposure is used, it is used before the virus is subjected to HPLC. In the methods of the present invention where the culture of AAV particles is treated with a detergent, the detergent can be any detergent such as, but not limited to octylglucopyranoside (OCG), CHAPS or deoxycholate. Other detergents, such as zwitterionic detergents could also be utilized. One of skill in the art would be able to utilize the teachings of the present invention to determine whether or not a particular detergent can be utilized to purify AAV2, AAV4 and/or AAV5. By testing a detergent at various pHs, the skilled artisan would know if a particular detergent was suitable for purification and at what pH the AAV particles should be treated.

The methods of the present invention where the culture of AAV particles is treated with a detergent are suitable for the purification of AAV2, AAV4 and AAV5 particles. In the methods of the present invention, benzonase or any other enzyme that digests DNA, such as a DNAse I can be added to the detergent. The concentration of benzonase or DNAse I utilized can range from about 10-100 µg/ml.

The present invention also provides a method of purifying adeno-associated virus 2 (AAV2) particles comprising: a) treating a culture of wild-type or recombinant AAV2 particles with at least about 1.5% octylglucopyranoside and; b) subjecting the culture of a) to high performance liquid chromatography (HPLC), wherein the particles are bound to an ion exchange column equilibrated at a pH of about 6.5 to about 7.0 and at a salt concentration of greater than 150 mM and wherein the AAV particles are eluted with about 100-400 mM salt in order to obtain purified AAV particles.

The present invention also provides a method of purifying AAV2 particles comprising: treating a culture of wild-type or recombinant AAV2 particles with at least about 0.1% octylglucopyranoside and benzonase and; b) subjecting the culture of a) to high performance liquid chromatography (HPLC), wherein the particles are bound to an ion exchange column equilibrated at a pH of about 6.5 to about 7.0 and at a salt concentration of greater than 150 mM and wherein the AAV particles are eluted with about 100-400 mM salt in order to obtain purified AAV particles.

The present invention further provides a method of purifying adeno-associated virus 4 (AAV4) comprising: a) treating a culture of wild-type or recombinant AAV4 particles with at least about 0.5% octylglucopyranoside (OCG) and benzonase; b) subjecting the culture of (a) to high performance liquid chromatography (HPLC), wherein the particles are bound to an ion exchange column equilibrated at a pH of about 6.7 to about 7.2 and at a salt concentration of greater than 150 mM, and wherein the AAV 4 particles are eluted with about 200-600 mM salt in order to obtain purified AAV 4 particles.

The present invention also provides a method of purifying adeno-associated virus 5 (AAV5) particles comprising: a) treating a culture of wild-type or recombinant AAV4 particles with at least about 1.5% octylglucopyranoside (OCG) and; b) subjecting the culture of (a) to high performance liquid chromatography (HPLC), wherein the particles are bound to an ion exchange column equilibrated at a pH of about 6.0 to about 6.5 and at a salt concentration of greater than 150 mM, and wherein the AAV 5 particles are eluted with about 150-400 mM salt in order to obtain purified AAV 5 particles.

AAV2 particles can also be purified by a method comprising a) treating a culture of wild-type or recombinant AAV2 particles with at least about 0.5% deoxycholate (DOC) and; subjecting the culture of (a) to high performance liquid chromatography (HPLC), wherein the particles are bound to an HS column equilibrated at a pH of about 5.5 to about 6.5 and at a salt concentration of greater than 150 mM and wherein the AAV particles are eluted with about 100-400 mM salt in order to obtain purified AAV particles.

AAV2 particles can also be purified by a method comprising a) treating a culture of wild-type or recombinant AAV2 particles with at least about 0.5% deoxycholate (DOC) and; subjecting the culture of (a) to high performance liquid chromatography (HPLC), wherein the particles are bound to a CM-Poros column equilibrated at a pH of about 5.5 to about 7.5 and at a salt concentration of greater than 150 mM and wherein the AAV particles are eluted with about 100-400 mM salt in order to obtain purified AAV particles.

AAV2 particles can also be purified by a method comprising a) treating a culture of wild-type or recombinant AAV2 particles with at least about 0.5% deoxycholate (DOC) and; subjecting the culture of (a) to high performance liquid chromatography (HPLC), wherein the particles are bound to an HQ column equilibrated at a pH of about 6.5 to about 7.5 and at a salt concentration of greater than 150 mM and wherein the AAV particles are eluted with about 100-300 mM salt in order to obtain purified AAV particles.

AAV4 particles can also be purified by a method comprising: a) treating a culture of wild-type or recombinant AAV4 particles with at least about 0.5% octylglucopyranoside (OCG) and benzonase; and b) subjecting the culture of (a) to high performance liquid chromatography (HPLC), wherein the particles are bound to an HQ column equilibrated at a pH of about 6.5 to about 7.5 and at a salt concentration of greater than 150 mM, and wherein the AAV 4 particles are eluted with about 200-600 mM salt in order to obtain purified AAV 4 particles.

AAV4 particles can also be purified by a method comprising: a) treating a culture of wild-type or recombinant AAV4 particles with at least about 0.5% octylglucopyranoside (OCG) and benzonase; and b) subjecting the culture of (a) to high performance liquid chromatography (HPLC), wherein the particles are bound to an HS column equilibrated at a pH of about 6.0 to about 7.0 and at a salt concentration of greater than 150 mM, and wherein the AAV 4 particles are eluted with about 200-600 mM salt in order to obtain purified AAV 4 particles.

The present invention also provides a population of AAV2 particles having a level of purity of greater than 50%, 55%, 50%, 65%, 70%, 75%, 80%, 85%, 90% or 95% purity.

Also provided by the present invention is a population of AAV4 particles having a level of purity of greater than 50%, 55%, 50%, 65%, 70%, 75%, 80%, 85%, 90% or 95% purity.

Further provided by the present invention is a population of AAV5 particles having a level of purity of greater than 50%, 55%, 50%, 65%, 70%, 75%, 80%, 85%, 90% or 95% purity.

The purity of the samples can be determined using a number of assays standard in the art. Additionally, as described in the Examples provided herein, contaminating proteins can be detected by SDS page of the samples and staining with SYPRO Red or silver. Alternatively, Moldi mass spectrometry can be used to assess the purity of the samples. Plasmid or cellular DNA contaminants can be detected using quantitative PCR.

The virus in the final material can be detected and quantified using quantitative PCR of material treated with DNAse or Benzonase in order to determine the number of DNAse resistant particles in the preparation. Biologically active particles can be measured using a replication center assay as described in the literature for the detection of viruses in vitro (Clark et al., Human Gene Therapy 1995 6:1329-1341). Biological activity can also be measured by transducing cells in vitro and assaying for transgene activity. For example, recombinant AAV containing a beta galactosidase transgene can be assayed by staining the cells with Xgal. Alternatively, proteins produced by the recombinant AAV particles, such as human growth hormone and Factor IX can be assayed by ELISA.

The methods of the present invention are suitable for small scale as well as large scale purification of AAV particles. The methods can be practiced in a laboratory setting as well as in a large scale purification setting, such as in a manufacturing facility. The components necessary for purification of AAV particles can be provided in the form of a kit comprising an ion exchange column, equilibration buffer, wash buffer, elution buffer and a column for concentration of the AAV particles. Other components can include lysis buffer as well as detergent.

The present invention is more particularly described in the following examples which are intended as illustrative only since numerous modifications and variations therein will be apparent to those skilled in the art.

EXAMPLES

Production of rAAV

Recombinant AAV2, 4, 5 was produced using a three plasmid procedure previously described (Alisky et al., 2000). Briefly semi-confluent 293T cells are transfected by calcium phosphate with three plasmids; an Ad helper plasmid containing the VA RNA, E2, and E4, an AAV helper plasmid containing the Rep and Cap genes for the serotype that is to be packaged, a vector plasmid containing the ITRs corresponding to the serotypes flanking a reporter gene of interest. 48-hrs post transduction the cells are harvested by scraping in TD buffer (140 mM NaCl, 5 mM KCl, 0.7 mM $K_2HPO_4$, 25 mM Tris-HCl pH 7.4) and the cell pellet concentrated by low speed centrifugation.

Generation of Clarified Viral Lysate (CVL)

The cell pellet ($3 \times 10^8$ cells/plate) was resuspended in TD buffer ($2 \times 10^7$ cells/ml) and the cell lysate was frozen/thawed three times. Cellular debris was removed by centrifugation (2000×g). Detergent (e.g. octyl-gluco-pyranoside, 0.1% final AAV2; 0.5% final AAV4; 1.5% final AAV5) and benzonaze (except for AAV5) were added to the supernatant, the lysate was incubated at 37° C. for additional 30 minutes. Any residual debris was removed by centrifugation at 10,000×g for 5 mins. The resulting CVLs were used in all subsequent experiments. Protein yields were typically 4 to 6 mg/ml.

Purification of rAAV Using HPLC

A Biocad 700E high-performance liquid chromatography (HPLC) system (PerSeptive Biosystems, Framingham, Mass.) together with Poros resins (20 μm bead size) were used in the purification of rAAV. The column to be tested (1.7 ml bed volume) was equilibrated with 10 column volumes (CV) of 20 mM Hepes/20 mM MES/20 mM sodium acetate buffer of varying pH and the CVL (2 ml, 8-10 mg of protein) was applied at a flow rate of 10 ml/min, using the automated injector (Cobra) of the system. The column was washed with 5-10 CV of buffer containing no salt (0 M) and 5-10 CV of buffer containing 150 mM KCl and the flow through and wash fractions were collected. Bound material was eluted by application of 15 CV of a linear gradient (150 mM-1 M KCl) and 1.5 ml fractions were collected. All fractions were tested for rAAV in our transduction assay. Once the suitable column and pH were determined, the method was further improved by eluting the bound rAAV in salt steps rather than a gradient.

Concentration of rAAV

The elution fractions from the HPLC were pooled together. The eluate was applied to a centriplus filter (Millipore, 100 kDa cut off) and spun according to the manufacturer's instructions. The filter was washed once with a TD buffer, containing 0.5% deoxycholate, and a second time with a 25 mM Tris-HCl, pH 8 buffer and the rAAV was concentrated to 100-200 μl in the same buffer. After the purification and concentration procedure, the protein content of all fractions was determined using the Biorad protein assay and the purity of the various fractions was analyzed by a gradient (4-20%) sodium dodecyl sulphate-polyacrylamide gel electrophoresis (SDS-PAGE) and stained with SYPRO Red (Molecular Probes, Eugene, Oreg.). In addition, samples were analyzed by western blotting, using the B1 antibody (anti-AAV2) and anti-AAV4 and anti-AAV5 antibodies. The final purified stock was also tested for presence of plasmid DNA. Briefly, *E. coli* bacteria were transformed with serial dilutions of pUC plasmid (control), HPLC-purified or CsCl-purified AAV stock. Bacterial colonies were counted after 16 hours incubation at 37° C.

Transduction Assay

Exponentially growing COS cells were plated in a 96 well plate at 75% confluency. After allowing sufficient time for attachment, the cells were infected with adenovirus type 5 at a MOI of 10 and incubated for 1 hr at 37° C. 10 μl of each collected fraction was added to the corresponding well. After 24 hrs of incubation at 37° C., the cells were fixed and stained for beta-galactosidase activity overnight at 37° C. with 5-bromo-4-chloro-3-indolyl-β-d-galactopyranoside. Transduced cells were visually scored (blue cells) using a light microscope. For quantitation, COS cells were transduced in 10 fold serial dilution with the different fractions of purified AAV and stained 24 hr post infection. The titer was determined by identifying the dilution with less than 10 positive cells/well. Transducing units per milliliter of lysate were defined as the number of blue cells in the last dilution well multiplied by the dilution factor. All transduction assays were done in duplicate and were repeated if the difference between the two plates was greater than 10 fold.

Antibodies for Western Blotting

For use in western blots, polyclonal antibodies were generated against peptides from the capsid of AAV4 (TNFTLKRPTNFSN) and AAV5 (NGMTNNLQGSNTY) and then affinity purified by coupling the peptide to activated sepharose beads. Antibody to AAV2 was purchased from American Research products (B1).

Western Blotting

Western blotting was performed as described before. Briefly, equal amounts of protein from the pooled column fractions were separated on either a 4-12% or 4-20% gradient SDS PAGE, the proteins transferred onto a nitrocellulose membrane and the membrane probed with the corresponding antibody (anti-AAV5, anti-AAV4 and anti-AAV2 B1). The secondary antibody was anti-mouse IgG (for anti-AAV2, B1) or anti-rabbit IgG (for anti-AAV4 and anti-AAV5) conjugated to horseradish peroxidase (Amersham Life Sciences). The blot was developed using the enhanced chemiluminescence peroxidase substrate (ECL, Amersham).

Quantitative PCR

Encapsidated viral genomes were quantified using an ABI 7700 and a primer set specific for the RSV promoter in the vector Forward 5'-GATGAGTTAGCAACATGCCTTACAA Reverse 5'-TCGTACCACCTTACTTCCACCAA. Following a 10 min 95° C. activation step, a two step PCR cycle was run at 95° C. for 15 sec and 60° C. for 1 min for 40 cycles. Amplified sequence was detected using the SYBR green PCR universal master mix (ABI Foster City Calif.). Following the indicated treatment samples were subsequently treated with Benzonase (6000 units/ml) and incubated at 37° C. for 30 min, then digested with Protease K (40 mg/ml) for 1 hr. The DNA was extracted with phenol/chloroform, precipitated and resuspended in water. Typically 1 l of DNA was added to 25 l reaction. A standard curve was generated by serial dilution of a double banded CsCl purified plasmid standard.

EM Analysis

Electron micrographs of purified AAV were prepared by spreading virus on formvar coated copper grids. The dried grids were then negatively stained with 5% Uranyl Acetate for one minute. Following drying, the particles were visualized using a JEOL 100 CX-II TEM.

Purification Results

Initial experiments were aimed at generating a cleared viral lysate (CVL) that would give a high yield of transducing rAAV particles and at the same time could be used for chromatographic separation of the virus. To test a number of different conditions for preparing the CVL, $3 \times 10^8$ cells were pooled and processed together in the initial rounds of freeze/thaw (see above). After removal of cellular debris, the CVL was further treated as described in Table 1 and 0.5 ml of treated CVL was tested. A qualitative assessment of the biological activity of different preparations of rAAV2 is summarized in Table 1a. Table 1 shows the biological and binding properties of CVL preparations. All CVL treatments were assayed on the same plate in duplicate. The numbers shown are the total transducing units. All treatments were in TD buffer except where noted. Biological activity was determined using the transduction assay described in the Examples section. Treatments shown in bold were chosen for further chromatographic characterization.

A number of conditions produced similar levels of biological activity and a high rate of virus recovery after chromatography. Comparison of CVL prepared by three rounds of freeze/thaw lysis in either TD buffer or PBS buffer with or without benzonase all yield similar biological activity however only virus prepared in TD buffer produced material that could bind to an anion exchange column. The addition of detergent to the cell lysate improved the yield of the rAAV vector particles compared to only freeze-thaw treatment. However, the choice of detergent [NP40, octyl-gluco-pyranoside (OGP) or deoxycholate (DOC)] and its concentration had an effect on the binding of the particles to the ion-exchange resin. Although 0.5% DOC treatment gave the best yield of active AAV based on the transduction assay, CVL failed to bind completely when applied to the Poros PI column. The addition of benzonase (20 units/ml) to the 0.5% deoxycholate treatment resulted in material, which could be separated chromatographically, but the strong ionic nature of DOC made the material sensitive to benzonase and lowered the biological activity of the CVL. Addition of OGP at 1.5% alone or at 0.1% with 20 u/ml benzonase resulted in improved rAAV2 yields and 100% binding to the ion-exchange column.

Similarly, it was found that the addition of 0.5% OGP with 20u/ml benzonase to AAV4 CVL yielded high titers and 100% binding to ion-exchange columns. (Table 1b). Addition of deoxycholate to the AAV4 lysate slightly increased the transduction titer but the material failed to bind to the ion-exchange resin. 1.5% OGP alone or with benzonase treatment also increased the transduction titer of the starting material, but the CVL failed to bind to any of the ion-exchange resins tested. 0.1% OGP with or without exonuclease treatment was not enough to solubilize all of the AAV4 starting material. Treatment of the AAV4 lysate with 0.5% OGP and 20u/ml benzonase improved the transduction titer and the resulting CVL bound 100% to several ion-exchange resins (Table 1b).

Treatment of rAAV5 CVL with 1.5% OGP alone yielded high titer virus that efficiently bound to the ion-exchange resin. (Table 1c). Benzonase treatment of AAV5 lysate, regardless of detergent present resulted in loss of binding to the resins and all of the transducing virus was found in the flow through. Addition of DOC to the starting material lowered AAV5s biological activity (Table 1c).

A number of ion-exchange resins were tested for their ability to bind and elute AAV particles (Table 2). The CVL treatments shown in bold (table 1) was chosen for further chromatographic characterization. The criteria for evaluation of the different resins was their ability to bind 100% of the biological activity at a salt concentration equal to or greater than 150 mM NaCl (the salt of the CVL) and to be eluted from the column without any significant loss in transduction titer. CVLs prepared in TD buffer with less than 150 mM NaCl were found not to bind efficiently to the chromatography resins. The following columns were tested for binding and elution of all three serotypes: Poros PI and D50 (weak anion-exchange resins), HQ (strong anion-exchange resin), HS and S (strong cation-exchange resins), CM (weak cation-exchanger). In pilot experiments, each column was pH mapped and particle binding at non-saturating conditions was determined using a transduction assay. Recombinant AAV2 failed to bind to any of the cation-exchange resins and bound very weakly (below 140 mM NaCl, TD buffer) to both D50 and HQ. However, at pH above 6.2, washing the resin with 150-200 mM KCl buffer did not result in a significant loss of transduction and over 90% of the bound particles were eluted with 350 mM KCL.

Recombinant AAV4 also failed to bind any of the cation-exchange resins. But it interacted more tightly with PI at all pHs tested compared to AAV2 and eluted between 400 mM and 500 mM KCL (Table 2). The binding of AAV4 to HQ was weaker than to PI. At pH 7 and above, AAV4 bound at 150 mM NaCl and eluted at 350 mM KCL. Recombinant AAV5 bound to both PI and HQ regardless of pH but elution from the resins improved as the pH decreased (Table 2). Under these conditions AAV5 did not bind to any of the cation-exchange resins. In addition, Poros HP2, PE and ET (hydrophobic interaction columns) were tested for their ability to bind and elute AAV. It was found that under these conditions, these resins were not useful for purifying rAAV2, 4, or 5.

Because of stable binding at 150 mM NaCl and efficient elution with a high rate of recovery the weak anion-exchange resin PI was chosen for the initial step in purifying AAV: pH 6.7 for AAV2; pH 7 for AAV4; and pH 6.2 for AAV5. It was determined that for the purposes of AAV separation the capacity of the resin was approximately 3 milligram of protein per milliliter of PI . This single purification step yielded a 4,000-fold enrichment for each virus. Analysis by SDS-PAGE and detection with SYPRO Red identified a number of contaminating proteins that were less than 100 kDa in molecular weight. These proteins were removed and the virus concentrated by using a Centriplus 100 kDa filter. A final wash step with buffer, containing 0.5% DOC was sufficient to remove all contaminating proteins. As judged by, SYPRO Red staining (sensitivity, 1-10 ng of protein per band) the virus preparations were greater than 99% free of contaminating proteins.

Figure 2:
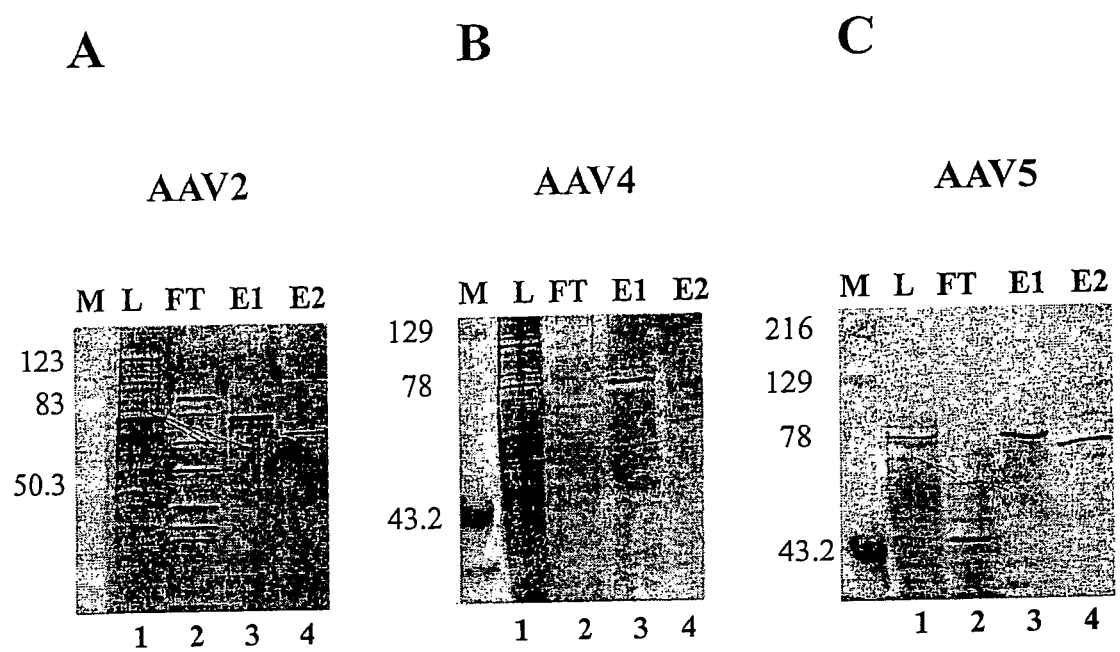
FIG. 2 shows SDS-PAGE analysis of HPLC- and Centriprep-purified fractions. Fractions from each purification step were pooled and resolved on a 4-20% gradient SDS-polyacrylamide gels. Protein bands were visualized using the SYPRO Red staining reagent (Molecular Probes, 1-10 ng of lower limit sensitivity). The image was captured using fluorescent scanning illumination (Storm PhosphoImager). Protein size marker lane in all three panels is designated with (M) and the corresponding molecular weights are shown on the right hand side of each gel. Lane 1 in all panels contains the cleared viral lysate or load (L, 2 µg); lane 2 contains the PI flow through (FT, 1 µg), lane 3 shows the proteins in the PI elution fraction (E1, 1 µg) and lane 4 shows the final purified material after concentration (E2, 0.5 µg). (A) AAV2 purification. (B) AAV4 purification. (C) AAV5 purification.
Figure 3:
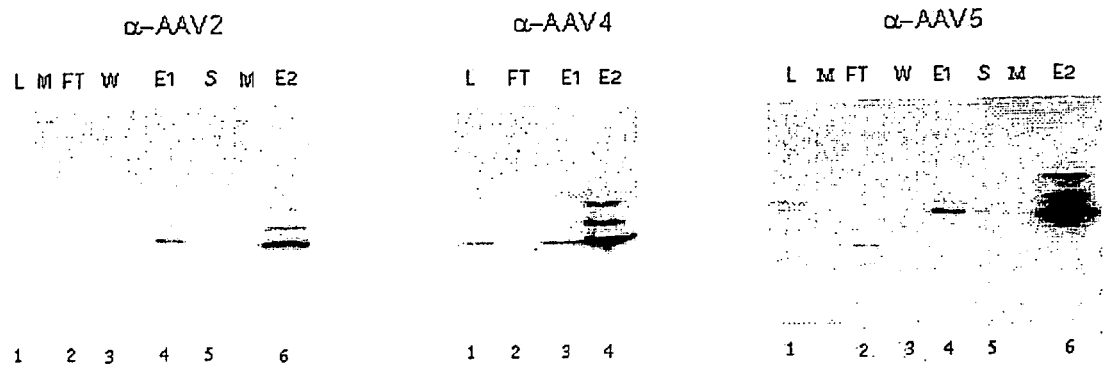
FIG. 3 shows western Blot analysis of HPLC- and Centriprep-purified fractions. Western blots of protein fractions separated on SDS gels performed using standard methods (Mendelson et al). (L) designates the viral lysate load lane; (M) designates the protein marker lane; (FT)—flow through; (W)—column wash fraction; (E1)—PI elution; (S)—2M NaCl wash fraction; (E2)—Centriprep concentrated final viral stock. The protein amounts separated in each gel are identical to those in FIG. 2. (A) Fractions were separated on 4-12% gradient gel and the membrane was probed with an anti-AAV2 Cap monoclonal antibody (B1 clone, 1:10 dilution, American Research Products). The secondary antibody was anti-mouse IgG conjugated to horseradish peroxidase (1:5000 dilution, Amersham); (B) Fractions were separated on 4-12% gradient gel and the blot was probed with an anti-AAV4 Cap polyclonal antibody (see Examples, 1:1000 dilution); (C) Fractions were separated on 4-20% gradient gel and the membrane was incubated with an anti-AAV5 polyclonal antibody (Examples, 1:2000 dilution). The secondary antibody for both (B) and (C) was anti-rabbit IgG conjugated to horseradish peroxidase (1:5000 dilution, Amerasham Life Sciences). All blots were developed using an enhanced chemiluminescence peroxidase substrate (ECL, Amersham Life Sciences).

The final purification scheme for all three serotypes is outlined in FIG. 1 and the analysis of rAAV purity at the different purification stages SDS-PAGE and SYPRO Red staining is shown in FIG. 2. The CVL load, 2 ml, (FIG. 2 Panel A, B, and C lane 1) was applied to the respective column at the indicated pHs (see above). The flow through (FIG. 2 lane 2) was collected and the columns washed with buffer containing 150 mM KCL. The viral particles were eluted from the column (lane 3, E1). This AAV enriched fraction still contains a number of contaminating proteins. In fact, the AAV capsid proteins could not be visualized at this point. The major protein band observed in lane E1 with a molecular weight of approximately 70 kDa is a cellular contaminant, and should not be confused with VP1. Therefore, the eluate was further purified and concentrated using Centriplus 100 filters (see Materials and Methods) (lane 4, E2). This step further purified the virus and yield particles that were essentially free of contaminating proteins. To confirm the observed polypeptides were AAV2, 4 and 5 capsid proteins and to check for capsid proteins in the flow through or wash fractions, western blot was performed using the B1 mouse monoclonal antibody for AAV2, and anti-AAV4 and anti-AAV5 polyclonal antibodies generated against capsid peptides. The results are shown in FIG. 3. The three capsid proteins are present only in the E1 and E2 fractions (lanes 4 and 6 for AAV2, lanes 3-4 for AAV4 and lanes 4 and 6 for AAV5) and very little viral proteins can be found in the flow through or wash fractions.

Recovery of transducing material was better than 100%. Compared with the crude CVL, the total number of transducing particles increased 2-10 fold in the final purified material. This phenomenon has previously been described for AAV2: biological activity of the virus increases with purity (Clark et al., 1999; Zolotukhin et al., 1999) O'Riordan et al., 2000). As the activity of the purified material increased, the particle-to-infectivity ratio decreased 100 fold for the purified virus compared to the crude CVL. These results are summarized in Table 3. Contaminating plasmid DNA (or fragments) present in the crude material could interfere with an accurate determination of the number of DNAse resistant particles present in this fraction. Treatment of cell lysate transfected with the AAV2RnLacZ plasmids alone contained less than 1% of the DNA detected in the cell lysate used in Table 3. Previous research has reported a ratio of 1:1:10 for the VP1, VP2, and VP3 for the AAV capsid proteins purified from infected cell lysate. This ratio was observed with the HPCL purified virus (FIG. 3). Quantitative PCR analysis of the DNAse resistant viral genomes indicated the final preparation contained $1 \times 10^{10}$ encapsidated genomes. This number is similar to the number of particles estimated based on the amount of protein in the final material and indicates this method of preparation yields predominantly full particles. A similar percentage of full particles were estimated for AAV4 and AAV5 (Table 3).

Figure 4:
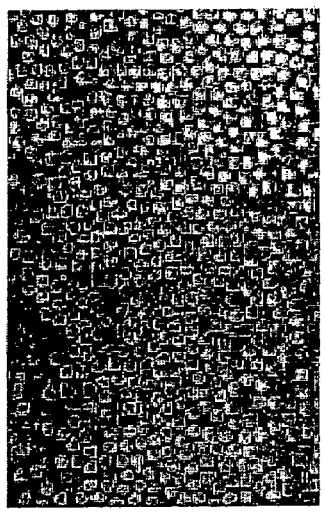
FIG. 4 shows the ultrastructure of HPLC-purified AAV5. Negatively stained CsCl-purified (A) or HPLC-purified (B) AAV5, analyzed by transmission electron microscopy, showing icosohedral shaped particles of approximately 20-25 nm. The electron micrograph identified both empty and full particles in the CsCl purified material compared to the HPLC purified material.

To confirm the percentage of full particle estimated by the protein and DNA determination of the purified material, electron micrographs of the purified virus were prepared (FIG. 4). Negatively stained preparations of the purified AAV5 showed icosohedral shaped particles of approximately 20-25 nm (FIG. 4B). Several fields were analyzed and the purified material was shown to contain greater than 90% full particles for all serotypes. This value is in agreement with that of the protein to genome ratio reported in Table 3. Negatively stained preparations of AAV5 purified by 1 round of CsCl isopycnic banding contained a number of empty particles compared to the HPLC (FIG. 4A).

The availability of high titer AAV2 stocks has dramatically increased our understanding of this virus and its utility as a gene transfer vector. The investigation of the binding properties of the capsid has led to the development of affinity purification methods based on this interaction. These methods of purification use iodexanol gradients, either alone or in combination with heparin affinity chromatography or sulphate ion exchange chromatography to isolate AAV2. Although these methods are a significant improvement over CsCl gradient centrifugation, they are not readily amenable for large-scale commercial production. While all of the dependoviruses share a similar size and structure and dependence upon a helper virus for replication, their capsids have different sequences and possess different binding activities and thus different tissue tropism. Therefore all current methods incorporating a heparin affinity purification step would only be useful for production of AAV2 but not for other serotypes such as AAV4 or AAV5.

Several reports have demonstrated the utility of AAV4 and AAV5 as vectors for gene transfer. To further the evaluation of AAV4 and AAV5 the present invention provides efficient, scalable purification methods for these viruses. The procedures are based on ion-exchange chromatography, followed by a size separation/concentration step. The method is fast and generates essentially homogeneous material. Moreover, it is easily amenable for the purification of all six serotypes.

Virus particles were purified over 4000 fold from crude cell lysate using a two-step procedure. Freeze/thaw lysate was soulblized with OGP and the virus enriched over 200 fold by anion exchange chromatograph (PI resin). The choice of OGP over other detergents was based on improved biological activity of the starting CVL as well as chromatographic compatibility with DNAse treatment (Table 1). The PI eluate showed 2-10 fold improved biological activity while retaining only 10% of the starting viral genomes as judged by Q-PCR (Table 3). However, the PI fractions still contained a number of contaminating proteins (FIG. 2) and the eluate was further purified and concentrated by use of a high molecular weight retention filter. The resulting material consisted of greater than 90% AAV particles as shown by SYPRO Red staining of an SDS PAGE and western blot analysis of all collected fractions (FIGS. 2 and 3). Electron micrographs and measurement of the protein to DNA ratio both indicate there is less than 10% empty particles (FIG. 4B), compared to CsCl-purified preparations (FIG. 4A). While this method is effective at purifying biologically active particles it is not clear what the mechanism is for removing the non-transducing particles. One possibility is the non-transducing particles are not assembled correctly and therefore do not interact with the PI resin at the same pH as the active particles or are less stable and fall apart when subjected to treatment with deoxycholate and size exclusion filtration. More importantly, the particle-to-infectivity ratio dramatically decreased as the purity of the viral material increased (Table 3). These values are similar to ones reported for AAV2 purified via affinity chromatography. This improved ratio of full to empty particles should improve the therapeutic index of the virus preparations and reduce the contamination of the virus with defective competing and potentially immunogenic material. Finally, this method is easily scalable and fast. Using a 90 ml PI column, we routinely purify $10^{13}$ rAAV particles in 3 hrs.

AAV vectors have great potential as tools for gene delivery. The helper dependency combined with reports of stable transduction and minimal host immune response against the transduced cells has made AAV2 an attractive vector for gene therapy. The availability of highly purified AAV4 and AAV5 virus is an important step in the evaluation of these serotypes as vectors for gene transfer.

Throughout this application, various publications are referenced. The disclosures of these publications in their entireties are hereby incorporated by reference into this application in order to more fully describe the state of the art to which this invention pertains.

REFERENCES

ALEXANDER, I. E., RUSSELL, D. W., and MILLER, D. A. (1994). DNA-damaging agents greatly increase the transduction of Nondividing cells by adeno-associated virus vectors. J. Virol. 68, 8282-8287.

ALISKY, J. M., HUGHES, S. M., SAUTER, S. L., JOLLY, D., DUBENSKY, T. W., JR., STABER, P. D., CHIORINI, J. A., and DAVIDSON, B. L. (2000). Transduction of murine cerebellar neurons with recombinant FIV and AAV5 vectors [In Process Citation]. Neuroreport 11, 2669-2673.

AURICCHIO, A., O'CONNOR, E., HILDINGER, M., and WILSON, J. M. (2001). A single-step affinity column for purification of serotype-5 based adeno-associated viral vectors. Mol Ther 4, 372-374.

CHIORINI, J. A., KIM, F., YANG, L., and KOTIN, R. M. (1999). Cloning and characterization of adeno-associated virus type 5. J Virol 73, 1309-1319.

CHIORINI, J. A., YANG, L., LIU, Y., SAFER, B., and KOTIN, R. M. (1997). Cloning of adeno-associated virus type 4 (AAV4) and generation of recombinant AAV4 particles. J Virol 71, 6823-6833.

CLARK, K. R., LIU, X., MCGRATH, J. P., and JOHNSON, P. R. (1999). Highly purified recombinant adeno-associated virus vectors are biologically active and free of detectable helper and wild-type viruses. Hum Gene Ther 10, 1031-1039.

FLANNERY, J. G., ZOLOTUKHIN, S., VAQUERO, M. I., LAVAIL, M. M., MUZYCZKA, N., and HAUSWIRTH, W. W. (1997). Efficient photoreceptor-targeted gene expression in vivo by recombinant adeno-associated virus. Proc Natl Acad Sci U.S.A. 94, 6916-6921.

KALUDOV, N., BROWN, K. E., WALTERS, R. W., ZABNER, J., and CHIORINI, J. A. (2001). Adeno-associated virus serotype 4 (AAV4) and AAV5 both require sialic acid binding for hemagglutination and efficient transduction but differ in sialic acid linkage specificity. J Virol 75, 6884-6893.

KAPLITT, M. G., LEONE, P., SAMULSKI, R. J., XIAO, X., PFAFF, D. W., O'MALLEY, K. L., and DURING, J. M. (1994). Long term gene expression and phenotypic correction using adeno-associated virus vectors in the mammalian brain. Nature Genetics 8, 148-154.

McCOWN, T. J., XIAO, X., LI, J., BREESE, G. R., and SAMULSKI, R. J. (1996). Differential and persistent expression patterns of CNS gene transfer by an adeno-associated virus (AAV) vector. Brain Res 713, 99-107.

O'RIORDAN, C. R., LACHAPELLE, A. L., VINCENT, K. A., and WADSWORTH, S. C. (2000). Scaleable chromatographic purification process for recombinant adeno-associated virus (rAAV). J Gene Med 2, 444-454.

RUSSELL, D. W., MILLER, A. D., and ALEXANDER, I. E. (1994). Adeno-associated virus vectors preferentially transduce cells in S phase. Proc. Natl. Acad. Sci. U.S.A. 91, 8915-8919.

RUTLEDGE, E. A., HALBERT, C. L., and RUSSELL, D. W. (1998). Infectious clones and vectors derived from adeno-associated virus (AAV) serotypes other than AAV type 2. J Virol 72, 309-319.

SNYDER, R. O., MIAO, C. H., PATIJN, G. A., SPRATT, S. K., DANOS, O., NAGY, D., GOWN, A. M., WINTHER, B., MEUSE, L., COHEN, L. K., THOMPSON, A. R., and KAY, M. A. (1997). Persistent and therapeutic concentrations of human factor IX in mice after hepatic gene transfer of recombinant AAV vectors. Nat Genet 16, 270-276.

XIAO, X., LI, J., and SAMULSKI, R. J. (1996). Efficient long-term gene transfer into muscle tissue of immunocompetent mice by adeno-associated virus vector. J Virol 70, 8098-8108.

ZOLOTUKHIN, S., BYRNE, B. J., MASON, E., ZOLOTUKHIN, I., POTTER, M., CHESNUT, K., SUMMERFORD, C., SAMULSKI, R. J., and MUZYCZKA, N. (1999). Recombinant adeno-associated virus purification using novel methods improves infectious titer and yield. Gene Ther 6, 973-985.

TABLE 1a

| Treatment of AAV2 CVL | Transducing Units | Binding to Ion-exchange Column (PI) |
|---|---|---|
| no treatment (TD Buffer) | 1.00E+08 | 100% |
| no treatment (PBS Buffer) | 1.00E+08 | <10% |
| benzonaze | 2.00E+08 | <50% |
| 1% NP40 | 1.00E+08 | <50% |
| 0.5% DOC | 1.00E+08 | <80% |
| 2% DOC | 1.00E+07 | <10% |
| 0.5% DOC + benzonaze | 7.00E+07 | 100% |
| 2% DOC + benzonaze | 5.00E+07 | 100% |
| 1.5% OGP | 3.00E+08 | 100% |
| 0.1% Octylglucopyranoside (OGP) + benzonase | 3.00E+08 | 100% |
| 0.22 µm filter | 1.00E+08 | <10% |

TABLE 1b

| Treatment of AAV4 CVL | Transducing Units | Binding to Ion-exchange Column (PI) |
|---|---|---|
| no treatment (TD Buffer) | 1.00E+07 | 100% |
| 0.5% DOC | 1.00E+07 | <80% |
| 2% DOC | 1.00E+07 | <10% |
| 2% DOC + benzonase | 2.00E+07 | <50% |

TABLE 1b-continued

| Treatment of AAV4 CVL | Transducing Units | Binding to Ion-exchange Column (PI) |
|---|---|---|
| 1.5% OGP | 3.00E+07 | <50% |
| 0.1% OGP + benzonase | 5.00E+06 | 100% |
| 0.5% OGP + benzonase | 2.00E+07 | 100% |
| 1.5% OGP + benzonase | 5.00E+07 | <50% |

TABLE 1c

| Treatment of AAV5 CVL | Transducing Units | Binding to Ion-exchange Column (PI) |
|---|---|---|
| no treatment (TD Buffer) | 4.00E+07 | 100% |
| 0.5% DOC | 1.00E+07 | <80% |
| 1% DOC | 1.00E+07 | <50% |
| 2% DOC | 1.00E+07 | <10% |
| 2% DOC + benzonase | 1.00E+06 | <50% |
| 1.5% OGP | 8.00E+07 | 100% |
| 0.1% OGP + benzonase | 5.00E+06 | <50% |
| 1.5% OGP + benzonase | 5.00E+07 | <50% |

TABLE 2

| | pH map | salt at binding, (mM) | salt at elution, (mM) | Infectious Units % recovery |
|---|---|---|---|---|
| AAV2 | | | | |
| PI | 6.2 | <150 | 150-350 | <50 |
| | 6.5 | >150 | 150-350 | <90 |
| | 6.7 | >150 | 150-350 | >90 |
| | 7 | >150 | 200-350 | >50 |
| | 7.2 | >150 | 200-350 | >50 |
| HQ | 6.2 | <150 | 100-200 | >50 |
| | 6.5 | <150 | 100-200 | >50 |
| | 6.7 | <150 | 140-250 | >50 |
| | 7 | <150 | 140-250 | >50 |
| | 7.2 | <150 | 140-250 | >50 |
| AAV4 | | | | |
| PI | 6.2 | >150 | 700-900 | <50 |
| | 6.5 | >150 | 700-900 | <50 |
| | 6.7 | >150 | 600-700 | <70 |
| | 7 | >150 | 400-500 | >90 |
| | 7.2 | >150 | 500-600 | >90 |
| HQ | 6.2 | <150 | 150-300 | <50 |
| | 6.5 | <150 | 150-350 | <50 |
| | 6.7 | <150 | 150-350 | <50 |
| | 7 | >150 | 200-350 | >90 |
| | 7.2 | >150 | 200-350 | >80 |
| AAV5 | | | | |
| PI | 6.2 | >150 | 150-350 | >90 |
| | 6.5 | >150 | 250-400 | <90 |
| | 6.7 | >150 | 200-350 | <90 |
| | 7 | >150 | 200-350 | >80 |
| | 7.2 | >150 | 200-350 | >80 |
| HQ | 6.2 | >150 | 300-500 | <70 |
| | 6.5 | >150 | 300-500 | <70 |
| | 6.7 | >150 | 300-500 | <80 |
| | 7 | >150 | 250-450 | <90 |
| | 7.2 | >150 | 250-450 | <90 |

TABLE 3

| AAV Serotype | Purification Step | Particles ($10^9$) | Infectious Units ($10^6$) | Particles % recovery | Infectious Units % recovery | Protein (mg)/ (estimated particles) | Particle-to-Infectivity Ratio |
|---|---|---|---|---|---|---|---|
| AAV2 | 3x freeze/thaw lysate, OG, benzonase | 500 | 40 | 100 | 100 | 4.2 | 12500 |
| | PI, pH 6.7 | 45.8 | 54 | 9 | 135 | 0.02 | 848 |
| | size-exclusion and concentration | 9.6 | 80 | 2 | 200 | 0.00007/ ($1.05 \times 10^{10}$) | 120 |
| AAV4 | 3x freeze/thaw lysate, OG, benzonase | 450 | 2 | 100 | 100 | 5.6 | 225000 |
| | PI, pH 7 | 47.2 | 21 | 10.5 | 1050 | 0.03 | 2248 |
| | size-exclusion and concentration | 2.7 | 20 | 0.6 | 1000 | 0.00002/ ($3.1 \times 10^9$) | 235 |
| AAV5 | 3x freeze/thaw lysate, OG | 2100 | 4 | 100 | 100 | 3.4 | 525000 |
| | PI, pH 6.2 | 310 | 8.4 | 15 | 210 | 0.01 | 36904 |
| | size-exclusion and concentration | 133 | 10 | 6.3 | 250 | 0.001/ ($1.5 \times 10^{11}$) | 13300 |

TABLE 4

| Treatment | Serotype | Ion-exchange resin | pH | Salt (mM) |
|---|---|---|---|---|
| No treatment (TD buffer) | AAV2 | HS | 5.5-6.5 | 100-400 |
| | | CM | 6.0-7.0 | 100-400 |
| | | HQ | 6.5-7.5 | 100-300 |
| No treatment (PBS Buffer) | AAV2 | HS | 5.5-7.5 | No binding |
| | | CM | 5.5-7.5 | No binding |
| | | HQ | 5.5-7.5 | No binding |
| 0.5% DOC | AAV2 | HS | 5.5-6.5 | 100-400 |
| | | CM | 6.0-7.0 | 100-400 |
| | | HQ | 6.5-7.5 | 100-300 |
| No treatment (TD buffer) | AAV4 | HS | 6.0-7.0 | 200-600 |
| | | HQ | 6.5-7.5 | 200-600 |
| 0.5% OG + benzonase | AAV4 | HS | 6.0-7.0 | 200-600 |
| | | HQ | 6.5-7.5 | 200-600 |
| No treatment (TD buffer) | AAV5 | HS | No Binding | No Binding |
| | | S | No Binding | No Binding |
| 0.5% DOC + benzonaze | AAV5 | HS | No Binding | No Binding |
| | | S | No Binding | No Binding |
| 0.5% DOC | AAV5 | HS | No Binding | No Binding |
| | | S | No Binding | No Binding |

TABLE 5

| | Infectious Units | Binding to Ion-exchange Column (PI) | pH | Salt (mM) |
|---|---|---|---|---|
| Treatment of AAV2 CVL | | | | |
| no treatment (TD Buffer) | 1.00E+08 | 100% | 6.0-7.0 | 100-400 |
| no treatment (PBS Buffer) | 1.00E+08 | <10% | 5.5-7.0 | |
| benzonase | 2.00E+08 | <50% | 5.5-7.0 | |
| 1% NP40 | 1.00E+08 | <50% | 5.5-7.0 | |
| 2% DOC | 1.00E+07 | <10% | 5.5-7.0 | |
| 0.5% DOC + benzonase | 7.00E+07 | 100% | 6.5-7.0 | 100-400 |
| 2% DOC + benzonase | 5.00E+07 | 100% | 6.5-7.0 | 100-400 |
| 0.5% DOC | 1.00E+08 | <80% | 6.5-7.0 | |
| 0.1% Octylglucopyranoside (OGP) + benzonase | 3.00+08 | 100% | 6.5-7.0 | 100-400 |
| 1.5% OGP | 3.00E+08 | 100% | 6.5-7.0 | 100-400 |
| 0.22 μm filter | 1.00E+08 | <10% | 6.0-7.0 | |
| Treatment of AAV4 CVL | | | | |
| no treatment (TD Buffer) | 1.00E+07 | 100% | 6.7-7.2 | 200-600 |
| 2% DOC | 1.00E+07 | <10% | 6.5-7.5 | |
| 2% DOC + benzonase | 2.00E+07 | <50% | 6.5-7.5 | |
| 0.5% DOC | 1.00E+07 | <80% | 6.5-7.5 | |
| 1.5% OGP + benzonase | 5.00E+07 | <50% | 6.5-7.5 | |
| 1.5% OGP | 3.00E+07 | <50% | 6.5-7.5 | |
| 0.1% OGP + benzonase | 5.00E+06 | 100% | 6.7-7.2 | 200-600 |
| 0.5% OGP + benzonase | 2.00E+07 | 100% | 6.7-7.2 | 200-600 |
| Treatment of AAV5 CVL | | | | |
| no treatment (TD Buffer) | 4.00E+07 | 100% | 6.0-6.5 | 100-400 |
| 2% DOC | 1.00E+07 | <10% | 6.0-6.5 | |
| 2% DOC + benzonase | 1.00E+06 | <50% | 6.0-6.5 | |
| 0.5% DOC | 1.00E+07 | <80% | 6.0-6.5 | |
| 1% DOC | 1.00E+07 | <50% | 6.0-6.5 | |
| 1.5% OGP + benzonase | 5.00E+07 | <50% | 6.0-6.5 | |
| 1.5% OGP | 8.00E+07 | 100% | 6.0-6.5 | 100-400 |
| 0.1% OGP + benzonase | 5.00E+06 | <50% | 6.0-6.5 | |

What is claimed is:

1. A method of purifying adeno-associated virus (AAV) particles comprising:
   a) subjecting a culture of wild-type or recombinant AAV particles to high performance liquid chromatography (HPLC), wherein the particles are bound to an ion exchange column equilibrated at a pH of about 6.0 to about 7.2 and at a salt concentration of greater than 100 mM, and wherein the AAV particles are eluted with about 100-600 mM salt in order to obtain purified AAV particles, wherein the culture is not subjected to iodixanol gradient separation;
   b) concentrating the eluted AAV particles; and
   c) washing the concentrated AAV particles.

2. The method of claim 1, wherein the ion exchange column is a strong anionic exchange column.

3. The method of claim 1, wherein the ion exchange column is a weak anionic exchange column.

4. The method of claim 1, wherein the ion exchange column is a strong cationic exchange column.

5. The method of claim 1, wherein the ion exchange column is a weak cationic exchange column.

6. The method of claim 1, wherein the ion exchange column is a weak ion exchange column having a surface coated with a resin selected from the group consisting of polyethyleneimine that is capable of surface ionization up to a pH of about 9, a styrene-divinylbenzene copolymer containing sulfonic acid groups, and a dextran matrix functionalized by diethylaminoethyl.

7. The method of claim 1, wherein the column is equilibrated with NaCl.

8. The method of claim 1, wherein the AAV particles are eluted with KCl.

9. A method of purifying adeno-associated virus (AAV) particles comprising:
   a. treating a culture of wild-type or recombinant AAV particles with a detergent;
   b. subjecting the culture of (a) to high performance liquid chromatography (HPLC), wherein the particles are bound to an ion exchange column equilibrated at a pH of about 6.0 to about 7.2 and at a salt concentration of greater than 100 mM and wherein the AAV particles are eluted with about 150-500 mM salt in order to obtain purified AAV particles, wherein the culture is not subjected to iodixanol gradient separation;
   c. concentrating the eluted AAV particles; and
   d. washing the concentrated AAV particles.

10. The method of claim 9, wherein the ion exchange column is a strong anionic exchange column.

11. The method of claim 9, wherein the ion exchange column is a weak anionic exchange column.

12. The method of claim 9, wherein the ion exchange column is a strong cationic exchange column.

13. The method of claim 9, wherein the ion exchange column is a weak cationic exchange column.

14. The method of claim 9, wherein the ion exchange column is a weak anionic exchange column having a surface coated with a resin selected from the group consisting of polyethyleneimine that is capable of surface ionization up to a pH of about 9, a styrene-divinylbenzene copolymer containing sulfonic acid groups, and a dextran matrix functionalized by diethylaminoethyl.

15. The method of claim 9, wherein the AAV particles are AAV2 particles, wherein the detergent is octylglucopyranoside (OCG) and wherein the concentration of octylglucopyranoside is at least about 1.5%.

16. The method of claim 9, wherein the AAV particles are AAV2 particles and wherein the ion exchange column is equilibrated at a pH of about 6.2 to about 7.2.

17. The method of claim 9, wherein the AAV particles are AAV2 particles and wherein the AAV2 particles are eluted with about 100-400 mM salt.

18. The method of claim 9, wherein the AAV particles are AAV2 particles, wherein the detergent is OCG and wherein the concentration of OCG is at least about 0.1% and further comprising benzonase.

19. The method of claim 9, wherein the benzonase is at about 20 µml.

20. The method of claim 19, wherein the ion exchange column is equilibrated at a pH of about 6.2 to about 7.2.

21. The method of claim 20, wherein the AAV2 particles are eluted with 100-400 mM salt.

22. The method of claim 9, wherein the AAV particles are AAV4 particles, wherein the detergent is OCG and wherein the concentration of OCG is about 0.5% and further comprising benzonase.

23. The method of claim 22, wherein the concentration of benzonase is at least about 20 µ/ml.

24. The method of claim 9, wherein the AAV particles are AAV4 particles and wherein the ion exchange column is equilibrated at a pH of about 6.7 to about 7.2.

25. The method of claim 9, wherein the AAV particles are AAV4 particles and wherein the AAV4 particles are eluted with about 200-600 mM salt.

26. The method of claim 9, wherein the AAV particles are AAV5 particles, wherein the detergent is OCG and wherein the concentration of OCG is about 1.5%.

27. The method of claim 9, wherein the AAV particles are AAV5 particles and wherein the ion exchange column is equilibrated at a pH of about 6.0 to about 7.2.

28. The method of claim 9, wherein the AAV particles are AAV5 particles and wherein the AAV5 particles are eluted with about 100-400 mM salt.

29. The method of claim 9, wherein the AAV particles are adeno-associated virus 2 (AAV2) particles comprising:
   a. treating a culture of wild-type or recombinant AAV2 particles with at least about 1.5% octylglucopyranoside (OCG) and;
   b. subjecting the culture of (a) to high performance liquid chromatography (HPLC), wherein the particles are bound to an ion exchange column equilibrated at a pH of about 6.5 to about 7.2 and at a salt concentration of greater than 150 mM and wherein the AAV2 particles are eluted with about 100-400 mM salt in order to obtain purified AAV2 particles.

30. The method of claim 29, wherein the ion exchange column is a strong anionic exchange column.

31. The method of claim 29, wherein the ion exchange column is a weak anionic exchange column.

32. The method of claim 30, wherein the strong anionic exchange column has a surface coated with quaternized polyethyleneimine with a surface ionization over a pH range of about 1 to about 14.

33. The method of claim 31, wherein the weak anionic exchange column has a surface coated with a resin selected from the group consisting of polyethyleneimine that is capable of surface ionization up to a pH of about 9, a styrene-divinylbenzene copolymer containing sulfonic acid groups, and a dextran matrix functionalized by diethylaminoethyl.

34. The method of claim 9, wherein the AAV particles are adeno-associated virus 2 (AAV2) particles comprising:
   a. treating a culture of wild-type or recombinant AAV2 particles with at least about 0.1% octylglucopyranoside (OCG) and about 20 µ/ml benzonase and;
   b. subjecting the culture of (a) to high performance liquid chromatography (HPLC), wherein the particles are bound to an ion exchange column equilibrated at a pH of about 6.5 to about 7.2 and at a salt concentration of greater than 150 mM and wherein the AAV2 particles are eluted with about 100-400 mM salt in order to obtain purified AAV2 particles.

35. The method of claim 34, wherein the ion exchange column is a strong anionic exchange column.

36. The method of claim 34, wherein the ion exchange column is a weak anionic exchange column.

37. The method of claim 35, wherein the strong anionic exchange column has a surface coated with quaternized polyethyleneimine with a surface ionization over a pH range of about 1 to about 14.

38. The method of claim 36, wherein the weak anionic exchange column has a surface coated with a resin selected from the group consisting of polyethyleneimine that is capable of surface ionization up to a pH of about 9, a styrene-divinylbenzene copolymer containing sulfonic acid groups, and a dextran matrix functionalized by diethylaminoethyl.

39. The method of claim 9, wherein the AAV particles are adeno-associated virus 4(AAV4) particles comprising:
  a. treating a culture of wild-type or recombinant AAV4 particles with at least about 0.5% octylglucopyranoside (OCG) and 20 µ/ml benzonase;
  b. subjecting the culture of (a) to high performance liquid chromatography (HPLC), wherein the particles are bound to an ion exchange column equilibrated at a pH of about 6.7 to about 7.2 and at a salt concentration of greater than 150 mM, and wherein the AAV 4 particles are eluted with about 200-600 mM salt in order to obtain purified AAV 4 particles.

40. The method of claim 39, wherein the ion exchange column is a strong anionic exchange column.

41. The method of claim 39, wherein the ion exchange column is a weak anionic exchange column.

42. The method of claim 40, wherein the strong anionic exchange column has a surface coated with quaternized polyethyleneimine with a surface ionization over a pH range of about 1 to about 14.

43. The method of claim 41, wherein the weak anionic exchange column has a surface coated with a resin selected from the group consisting of polyethyleneimine that is capable of surface ionization up to a pH of about 9, a styrene-divinylbenzene copolymer containing sulfonic acid groups, and a dextran matrix functionalized by diethylaminoethyl.

44. The method of claim 9, wherein the AAV particles are adeno-associated virus 5(AAV5) particles, comprising:
  a. treating a culture of wild-type or recombinant AAV4 particles with at least about 1.5% octylglucopyranoside (OCG) and;
  b. subjecting the culture of (a) to high performance liquid chromatography (HPLC), wherein the particles are bound to an ion exchange column equilibrated at a pH of about 6.0 to about 7.2 and at a salt concentration of greater than 150 mM, and wherein the AAV 5 particles are eluted with about 100-400 mM salt in order to obtain purified AAV 5 particles.

45. The method of claim 44, wherein the ion exchange column is a strong anionic exchange column.

46. The method of claim 44, wherein the ion exchange column is a weak anionic exchange column.

47. The method of claim 45, wherein the strong anionic exchange column has a surface coated with quaternized polyethyleneimine with a surface ionization over a pH range of about 1 to about 14.

48. The method of claim 46, wherein the weak anionic exchange column has a surface coated with a resin selected from the group consisting of polyethyleneimine that is capable of surface ionization up to a pH of about 9, a styrene-divinylbenzene copolymer containing sulfonic acid groups, and a dextran matrix functionalized by diethylaminoethyl.

49. A method of purifying AAV2 particles comprising:
  a. treating a culture of wild-type or recombinant AAV2 particles with at least about 0.5% deoxycholate (DOC) and;
  b. subjecting the culture of (a) to high performance liquid chromatography (HPLC), wherein the particles are bound to an HS column equilibrated at a pH of about 5.5 to about 6.5 and at a salt concentration of greater than 150 mM and wherein the AAV particles are eluted with about 100-400 mM salt in order to obtain purified AAV2 particles, wherein the culture is not subjected to iodixanol gradient seperation.

50. A method of purifying AAV2 particles comprising:
  a. treating a culture of wild-type or recombinant AAV2 particles with at least about 0.5% deoxycholate (DOC) and;
  b. subjecting the culture of (a) to high performance liquid chromatography (HPLC), wherein the particles are bound to a CM column equilibrated at a pH of about 5.5 to about 7.5 and at a salt concentration of greater than 150 mM and wherein the AAV particles are eluted with about 100-400 mM salt in order to obtain purified AAV particles, wherein the culture is not subjected to iodixanol gradient separation.

51. A method of purifying AAV2 particles comprising:
  a. treating a culture of wild-type or recombinant AAV2 particles with at least about 0.5% deoxycholate (DOC) and;
  b. subjecting the culture of (a) to high performance liquid chromatography (HPLC), wherein the particles are bound to an HQ column equilibrated at a pH of about 6.5 to about 7.5 and at a salt concentration of greater than 150 mM and wherein the AAV particles are eluted with about 100-300 mM salt in order to obtain purified AAV particles, wherein the culture is not subjected to iodixanol gradient separation.

52. A method of purifying AAV4 particles comprising:
  a. treating a culture of wild-type or recombinant AAV4 particles; with at least about 0.5% octylglucopyranoside (OCG) and benzonase; and
  b. subjecting the culture of (a) to high performance liquid chromatography (HPLC), wherein the particles are bound to an HQ column equilibrated at a pH of about 6.5 to about 7.5 and at a salt concentration of greater than 150 mM, and wherein the AAV 4 particles are eluted with about 200-600 mM salt in order to obtain purified AAV 4 particles, wherein the culture is not subjected to iodixanol gradient separation.

53. A method of purifying adeno-associated virus (AAV) particles comprising:
  a. subjecting a clarified viral lysate of wild-type or recombinant AAV particles to high performance liquid chromatography (HPLC), wherein the particles are bound to an ion exchange column equilibrated at a pH of about 6.0 to about 7.2 and at a salt concentration of greater than 100 mM, and wherein the AAV particles are eluted with about 100-600 mM salt in order to obtain purified AAV particles;
  b. concentrating the eluted AAV particles; and
  c. washing the concentrated AAV particles.

54. The method of claim 1, wherein the ion exchange column is a strong anionic exchange column having a surface coated with quaternized polyethyleneimine with a surface ionization over a pH range of about 1 to about 14.

55. The method of claim 9, wherein the ion exchange column is a strong anionic exchange column having a surface coated with quaternized polyethyleneimine with a surface ionization over a pH range of about 1 to about 14.

* * * * *